(12) United States Patent
Shusta et al.

(10) Patent No.: US 7,744,879 B2
(45) Date of Patent: Jun. 29, 2010

(54) BLOOD-BRAIN BARRIER TARGETING ANTIBODIES

(75) Inventors: Eric V. Shusta, Madison, WI (US); Xin X. Wang, Gaithersburg, MD (US); Yongku P. Cho, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 297 days.

(21) Appl. No.: 11/759,723

(22) Filed: Jun. 7, 2007

(65) Prior Publication Data

US 2008/0019984 A1 Jan. 24, 2008

Related U.S. Application Data

(60) Provisional application No. 60/811,618, filed on Jun. 7, 2006.

(51) Int. Cl.
*A61K 39/395* (2006.01)
*A61K 38/16* (2006.01)
*C12P 21/08* (2006.01)

(52) U.S. Cl. .............. 424/135.1; 424/134.1; 424/172.1; 514/12; 530/387.3

(58) Field of Classification Search ........................ None
See application file for complete search history.

(56) References Cited

U.S. PATENT DOCUMENTS 7,138,501 B2 * 11/2006 Ruben et al. ............ 530/388.23
2007/0009972 A1 * 1/2007 Chao et al. ................. 435/7.23

OTHER PUBLICATIONS

Wang et al. 2005. Book of Abstracts, 229th ACS National Meeting, Mar. 13-17, 2005, Abstract No. BIOT-359.*
Staddon J M et al., "P120, A P120-Related Protein (P100), and the Cadherin/Catenin Complex," Journal of Cell Biology, Rockefeller University Press, New York, US, US, vol. 130, No. 2, Jul. 1995, pp. 369-381.
Dixelius J et al., "Endostatin-induced tyrosine kinase signaling through the Shb Adaptor Protein Regulates Endothelial Cell Apoptosis," Blood, W. B. Saunders Company, Orlando, Fl, US, vol. 95, No. 11, Jun. 1, 2000, pp. 3403-3411.
Novak S et al., "A New Low Density Lipoprotein Receptor Homologue with 8 Ligand Binding Repeats in Brain of Chicken and Mouse." The Journal of Biological Chemistry May 17, 1996, vol. 271, No. 20, May 17, 1996, pp. 11732-11736.
Yamamoto T et al., "The Human LDL Receptor: A Cysteine-Rich Protein with Multiple ALU Sequences in its MRNA," Cell, Mit Press, Cambridge, MA, US, vol. 39 Nov. 1, 1984, pp. 27-38.
Duffy K R et al., "Human Blood-Brain Barrier Insulin-Like Growth Factor Receptor," Metabolism Clinical and Experimental Feb. 1988, vol. 37, No. 8, Feb. 1988, pp. 136-140.
Benjamin J Hackel et al., "Production of Soluble and Active Transferrin Receptor-Targeting Single-Chain Antibody Using *Saccharomyces cerevisiae*," Pharmaceutical Research, Kluwer Academic Publishers-Plenum Publishers, NE, vol. 23, No. 4, Mar. 25, 2006, pp. 790-797.
PCT/US2007/070587 Search Report; Jan. 14, 2008.
Verma et al., J Immunol Methods, Jul. 1, 1998, 216(1-2), 165-81.
Feldhaus et al., Nat. Biotechnol. 2003, 21(2), 163-70.
Wang et al., Nat. Methods, 2007, 4(2), 143-5.
Wu et al., Nat. Biotechnol., Sep. 23, 2005 (9), 1137-46.
Trail et al., Cancer Immunol Immunother, 2003, May 52(5), 328-37.
Saito et al., Adv Drug Deily Rev., Feb. 10, 2003;55(2), 199-215.
Sugano et al., Cancer Research, Dec. 2000, 6942-6949.
Martin et al., Analytical Chemistry News & Features, May 1998, 322-327.
Wang et al., J Immunol Methods, 2005, 304, 30-42.
Roux et al., J Cell Physiol, 1994, 159, 101-13.
Shusta et al., Nat Biotechnol., 2008, 18, 754-9.
Shusta et al., Nat Biotechnol., 1998, 16, 773-7.
Shusta el al., J Mol Biol., 1999, 292, 949-56.

* cited by examiner

*Primary Examiner*—Daniel E. Kolker
(74) *Attorney, Agent, or Firm*—Quarles & Brady, LLP

(57) ABSTRACT

This invention provides antibodies that bind brain endothelial cell receptors resulting in endocytosis/transcytosis of the receptor and bound ligands. In some embodiments, the ligand comprises the antibody in combination with a pharmaceutically active compound and the antibody directs delivery of the compound across the blood brain barrier (BBB). The invention also provides methods of identifying endothelial cell specific antibodies by panning the library against cultured cell monolayers. The invention further allows for identifying endothelial cell receptors that bind the antibody thereby providing target receptors against which to isolate further cognate ligands and their associated transport systems and by which to identify transcytosis transporters targeted by the antibodies.

6 Claims, 12 Drawing Sheets

Summary of RBE4-Binding scFv Clones.

| Class[a] | Unique Clones[b] | Human Germline Family Usage[c] | | # of Hits[d] | Seq ID No |
|---|---|---|---|---|---|
| 1 | A | VH3 | Vλ1 | 1468 | 1 |
| | B | VH3 | Vλ1 | 1 | 2 |
| | C | VH3 | Vλ1 | 1 | 3 |
| | G | VH3 | Vλ1 | 1 | 4 |
| | K | VH3 | Vλ1 | 1 | 5 |
| 2 | D | VH6 | Vλ1 | 159 | 6 |
| | I | VH6 | Vλ1 | 33 | 7 |
| | 4D90 | VH6 | Vλ1 | 1 | 8 |
| | 4D108 | VH6 | Vλ1 | 1 | 9 |
| 3 | F | VH3 | Vλ1 | 1 | 10 |
| 4 | H | VH6 | Vλ1 | 6 | 11 |
| | 4D47 | VH6 | Vλ1 | 1 | 12 |
| 5 | 4D84 | VH6 | Vλ1 | 1 | 13 |
| 6 | J | VH3 | None | 6 | 14 |
| 7 | E | VH3 | None | 1 | 15 |
| 8 | 4S46 | VH3 | None | 17 | 16 |
| 9 | 4D103 | VH3 | Vλ1 | 1 | 17 |
| 10 | 4S18 | VH4 | Vλ1 | 8 | 18 |
| | 4D98 | VH4 | Vλ1 | 1 | 19 |
| 11 | 4D46 | VH6 | Vλ1 | 2 | 20 |
| 12 | 4S21 | VH6 | Vλ1 | 2 | 21 |
| 13 | 4S25 | VH6 | Vλ1 | 1 | 22 |
| 14 | 4D80 | VH6 | Vλ1 | 14 | 23 |
| | 4D69 | VH6 | Vλ1 | 1 | 24 |
| | 4D128 | VH6 | Vλ1 | 4 | 25 |
| 15 | 4S53 | VH1 | Vκ3 | 1 | 26 |
| | 4D07 | VH1 | Vκ3 | 1 | 27 |
| | 4S30 | VH1 | Vκ3 | 1 | 28 |
| | 4D71 | VH1 | Vκ3 | 4 | 29 |
| 16 | 4D13 | VH1 | Vκ3 | 4 | 30 |
| 17 | 4S38 | VH2 | Vκ3 | 1 | 31 |
| 18 | 4S52 | VH6 | Vκ3 | 1 | 32 |
| | 4S69 | VH6 | Vκ3 | 2 | 33 |
| | 4D84 | VH6 | Vκ3 | 11 | 34 |

1760 of 2000 yeast clones investigated bind to RBE4 cells

FIG. 12

Multiple alignment of clone A like scFv clones

```
B   ASEVQLLESGGGLIQSGGSLRLSCAASGFTVTSNYMHWVRQAPGKGLEWVSLIYSGGSTS  60
G   ASEVQLLESGGGLIQSGGSLRLSCAASGFTVTSNYMHWVRQAPGKGLEWVSLIYSGGSTS  60
A   ASEVQLLESGGGLIQSGGSLRLSCAASGFTVTSNYMHWVRQAPGKGLEWVSLIYSGGSTS  60
C   ASEVQLLESGGGLIQSGGSLRLSCAASGFTVTSNYMHWVRQAPGKGLEWVSLIYSGGSTS  60
K   ASEVQLLESGGGLIQSGGSLRSPVQELCASPLTKNMMWVRQAKGKGLEWVSLIYSGGSTS  60
                                          *VHCDR1*          *VH(CDR2
B   YADSVKGRFTISRDNSKNTLYLQMNSLRAEDTAVYYCARGRPWYFDLWGRGTLVTVSSG  120
G   YADSVKGRFTISRDNSKNTLYLQMNSLRAEDTAVYYCARGRPWYFDLWGRGTLVTVSSG  120
A   YADSVKGRFTISRDNSKNTLYLQMNSLRAEDTAVYYCARGKPWYFDLWGRGTLVTVSSG  120
C   YADSVKGRFTISRDNSKNTLYLQMNSLRAEDTAVYYCARGRPWYFDLWGRGTVVTVSSG  120
K   KKXXVKGRFTISRDNSKNTLYLQMNSLRAEDTAVYYCARGXXXXXXXXXWGRGTVVTVSSG  120
                                          *VH(CDR3*
B   ILQSGGGGSGGGGSGGGGSQSVLTQPASVSGSPGQSITISCTGTSRDIGAYNYVSWYQQH  180
G   ILQSGGGGSGGGGSGGGGSQSVLTQPASVSGSPGQSITISCTGTSRDIGAYNYVSWYQQH  180
A   ILQSGGGGSGGGGSGGGGSQSVLTQPASVSGSPGQSITISCTGTSRDIGAYNYVSWYQQH  180
C   ILQSGGGGSGGGGSGGGGSQSVLTQPASVSGSPGQSITISCTGTSRDIGAYNYVSWYQQH  180
K   XKGSGGGGSGGGGSGGGGSQSVLTQPASVSGSPGQSITISCTXXXXXXXXXXXXXYYQQH  180
                                                *VL(CDR1*
B   PGKAPKVMIYDVSKRPSGVPDRFSGSKSGNTASLTISGLQAEDEADYYCSSYTNSSTPRV  240
G   PGKAPKVMIYDVSKRPSGVPDRFSGSKSGNTASLFLXGLQAEDEADYYCSSYTESSTPRV  240
A   PGKAPKVMIYDVSKRPSGVPDRFSGSKSGNTASLTISGLQAEDEADYYCSSYTGSSTPRV  240
C   PGKAPKVMIYDVSKRPSGVPDRFSGSKSANTASLTISGLQAEDEADYYCSSYTSSSTPRV  240
K   PGKAPKVMIYDXXXXXXXXVPDRFSGSKSGNTASLTISGLQAEDEADYYCXXXXXXXXXX  240
            *VL(CDR2*                                *VL(CDR3*
B   VFGGGTQLTVLSGIL  255
G   VFGGGTPLTVLSGIL  255
A   VFGGGTKLTVLSGIL  255
C   VFGGGTRVTVLSGIL  255
K   VFGGG-VLTVKXXX   254
```

FIG. 13

Multiple alignment of clone D like scFv clones:

```
D       ASQVQLQQSGPGLVKPSQTLSLTCAISGDSVSSHSYAPNWIRQSPSRGLEWLGMTYYRSK    60
I       ASQVQLQQSGPGLVKPSQTLSLTCDISGDSVSSHSAAPNWIRQSPSRGLEWLDTTYYRSK    60
H       ASSVQLQQGGTGLVKPSQTLSLTCDISGDSVSHSAAPNWIRQSPSRGLEWLGHTYYRSK    60
                                                VHCDR1              VHCDR2

D       WYNDYALSVKSRITINPDTSKNQFSLQLNSVTPEDTAIYYCARQLGGSGRDVWGQGTTVT   120
I       WYNDYALSVKSRITINPDTSKNQFSLHLNSVTPEDTAVYYCARQLGGSGRDVWGQGTTVT   120
H       KNNDYANSVKSRITINPDTSKNQFSLHLNSVTPEDTAVYYCARAMTRGIFDLWGRGTLVT   120
                                                        VHCDR3

D       VSSGSASAPTGILGSXXXXXXXXGGGGSGGGGSTELTQPTSASGTPGQRVTISCSGSSSIG   180
I       VSSGSASAPTGILGSXXXXXXXXGGGGSGGGGSTELTQPTSASGTPGQRVTISCSGSSSIG   180
H       VSSG--------ILGSXXXXXXGGGGSGGGGSQPVLTQSPSASGTPGQRVTISCSGSSSIG   173
                                                            VLCDR1

D       SRIYTYTQQLPGTAPKLLIYRNNQRPSVPDRFSGSKSGTSASLAISGLRSEDEADYYCA   240
I       SRIYTYTQQLPGTAPKLLIYRNNQRPSGVPDRFSGSKSGTSASLAISGLRSEDEADYYCA   240
H       SRIYTYNQQLKGTAPKLLIYRNNHRPSGVPDRFSGSKSGTSASLAISGLRSEDEADYYCA   233
                            VLCDR2

D       AWDILSGTVFGGGTQLFVLSGIL  264
I       AWDILSGTVFGGGTQLFVLSGIL  264
H       AWDILSGTVFGGGTQLFVLSGIL  257
        VLCDR3
```

FIG. 14

Multiple alignment of F with A-like clones:

```
A       ASEVQLLESGGGLIQSGGSLRLSCAASGFTVTSNYMSWVRQAPGKGLEWVS-LIYSGGST   59
C       ASEVQLLESGGGLIQSGGSLRLSCAASGFTVTSNYMSWVRQAPGKGLEWVS-LIYSGGST   59
B       ASEVQLLESGGGLIQSGGSLRLSCAASGFTVTSNYMSWVRQAPGKGLEWVS-LIYSGGST   59
G       ASEVQLLESGGGLIQSGGSLRLSCAASGFTVTSNYMSWVRQAPGKGLEWVS-LIYSGGST   59
K       ASEVQLLESGGGLIQSGGSLRSFVJPLSNPLTSNYMSWVRQAPGKGLEWVS-LIYSGGST   59
F       AEQVPLVESGGDLVQPGRSLRLSCAASGFDFQSSEMSWVRQPPGKGLEWVSHINSDGTN   60
                                    VHCDR1              VHCDR2

A       SYADSVKGRFTISRDNSRNTLYLQMNSLRAEDTAVYYCARGRPNWYFDLWGRGTLVTVSS  119
C       SYADSVKGRFTISRDNSRNTLYLQMNSLRAEDTAVYYCARGRPNWYFDLWGRGTLVTVSS  119
B       SYADSVKGRFTISRDNSRNTLYLQMNSLRAEDTAVYYCARGRPNWYFDLWGRGTLVTVSS  119
G       SYADSVKGRFTISRDNSRNTLYLQMNSLRAEDTAVYYCARGRPNWYFDLWGRGTLVTVSS  119
K       SYADSVKGRFTISRDNSRNTLYLQMNSLRAEDTAVYYCARGRPNWYFDLWGRGTLVTVSS  119
F       TYADSVKGRFTISRDNTRNSLYLQMDNLRPEDTALYYCVCRSSSFQEDFWQQTLVTVSS   120
                                                VHCDR3

A       GILGSGGGGSGGGGSGGGGSQSVLTQPASVSGSPGQSITISCTGTSRDIGAYNYVSWYQQ  179
C       GILGSGGGGSGGGGSGGGGSQSVLTQPASVSGSPGQSITISCTGTSRDIGAYNYVSWYQQ  179
B       GILGSGGGGSGGGGSGGGGSQSVLTQPASVSGSPGQSITISCTGTSRDIGAYNYVSWYQQ  179
G       GILGSGGGGSGGGGSGGGGSQSVLTQPASVSGSPGQSITISCTGTSRDIGAYNYVSWYQQ  179
K       GILGSGGGGSGGGGSGGGGSQSVLTQPASVSGSPGQSITISCTGTSRDIGAYNYVSWYQQ  179
F       GILGSGGGGSGGGGSGGGGSGGALIQPASVSGSPGQSITISCTGTSRDIGGNYVSWYQH   180
                                                            VLCDR1

A       HPGKAPKVMIYDVSKRPSGVPDRFSGSKSGHTASLTISGLQAEDEADYYCSSYTSSSTPR  239
C       HPGKAPKVMIYDVSKRPSGVPDRFSGSKSGHTASLTISGLQAEDEADYYCSSYTSSSTPR  239
B       HPGKAPKVMIYDVSKRPSGVPDRFSGSKSGHTASLTISGLQAEDEADYYCSSYTSSSTPR  239
G       HPGKAPKVMIYDVSKRPSGVPDRFSGSKSGHTASLTISGLQAEDEADYYCSSYTQSSTPR  239
K       HPGKAPKVMIYDVSKRPSGVPDRFSGSKSGHTASLTISGLQAEDEADYYCSSYTSSQSSP  239
F       HPGKAPKLIIYINSKRPSGVSNRFSGSKSGHTASLTISGLQAEDEADYYCGAY-TKTQQ   239
                    VLCDR2                                  VLCDR3

A       VVFGGGTKLTVLGGIL  255
C       VVFGGGTKVTVLGGIL  255
B       VVFGGGTYLTVLGGIL  255
G       VVFGGGTPPLTVLGGPL  255
K       CCFGGGL-PLTVXXXX  254
F       AVFGGGTKLTVLGGIL  255
```

FIG. 15

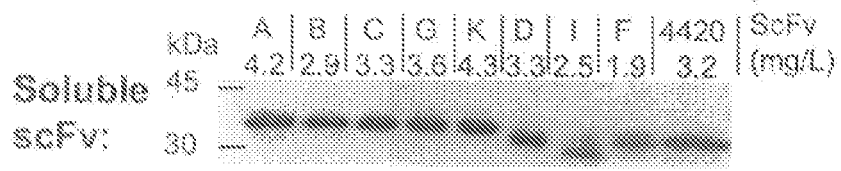
FIG. 16  ND: not determined.
| scFv Clones | RBE4 Binding | RBE4 Internalization |
|---|---|---|
| A | Yes | Yes |
| B | Yes | ND |
| C | Yes | ND |
| G | Yes | ND |
| K | Yes | ND |
| D | Yes | No |
| I | Yes | ND |
| H | ND | ND |
| F | Yes | No |
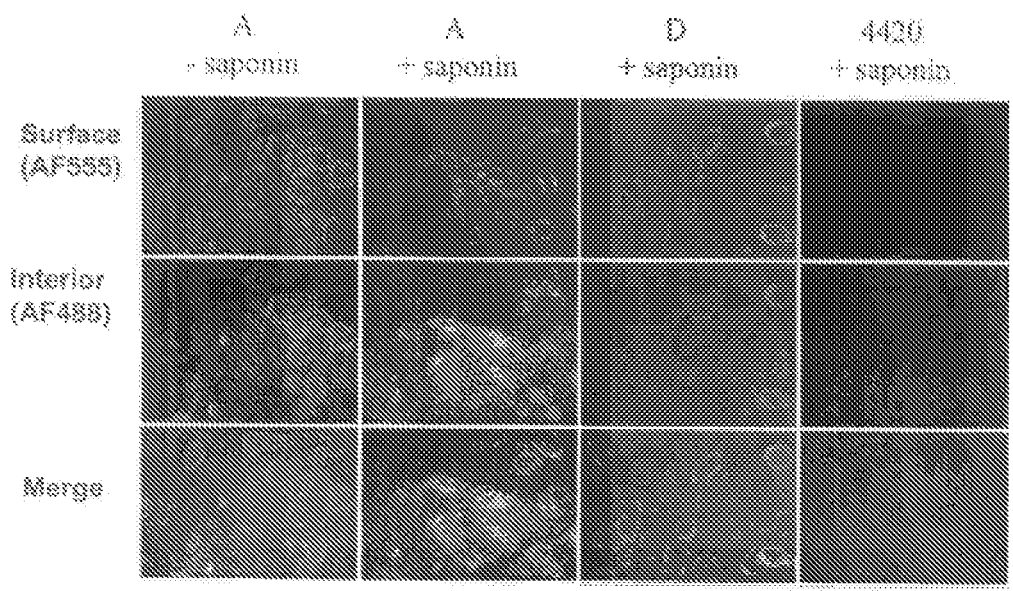
FIG. 17

BLOOD-BRAIN BARRIER TARGETING ANTIBODIES

CROSS REFERENCE TO RELATED APPLICATION

This non-provisional application claims the benefit of U.S. Provisional application 60/811,618, filed Jun. 7, 2006, which is incorporated herein by reference in its entirety for all purposes.

STATEMENT REGARDING FEDERALLY SPONSORED RESEARCH AND DEVELOPMENT

This work was supported in part by a grant from the National Institutes of Health NS052649. The Government of the United States may have certain rights in this invention.

FIELD OF THE INVENTION

This invention relates generally to antibodies recognizing endothelial cell surface receptors and methods of identifying such antibodies.

BACKGROUND OF THE INVENTION

Treatment modalities for brain and neurological diseases are extremely limited due to the impermeability of the brain's blood vessels to most substances carried in the blood stream. The blood vessels of the brain, referred to collectively as the blood-brain barrier (BBB), are unique when compared to the blood vessels found in the periphery of the body. Tight apposition of BBB endothelial cells (EC) to neural cells like astrocytes, pericytes and neurons induces phenotypic features that contribute to the observed impermeability. Tight junctions between ECs comprising the BBB limit paracellular transport, while the lack of pinocytotic vesicles and fenestrae limit non-specific transcellular transport. These factors combine to restrict molecular flux from the blood to the brain to those molecules that are less than 500 daltons and also lipophilic. Thus, using the large mass transfer surface area (over 21 $m^2$ from 400 miles of capillaries in human brain) of the bloodstream as a delivery vehicle is largely infeasible except in those circumstances where a drug with the desired pharmacological properties fortuitously possesses the size and lipophilicity attributes allowing it to pass freely through the blood vessel. Because of such restrictions, it has been estimated that greater than 98% of all small molecule pharmaceuticals and nearly 100% of the emerging class of protein and gene therapeutics do not cross the BBB.

In addition to the physical barrier presented by the BBB, efflux transporters such as p-glycoprotein (MDR1) and members of the multi-drug resistance-associated protein family (MRP) serve to further limit brain uptake of even those small molecules that are small and lipophilic. FIG. 1A is a micrograph of a section of rat brain (V=ventricle) illustrating the sequestration of horseradish peroxidase in vessels, while in small brain regions perfused by capillaries lacking the BBB, the protein diffuses readily into brain tissue. FIG. 2A also illustrates the impermeable nature of the BBB: histamine (111 Da) remains sequestered within the blood vessels and does not enter the brain interior.

Although neurological diseases such as brain cancer, Alzheimer's disease, Parkinson's disease, and stroke continue to afflict people worldwide, there has been a paucity of new therapies to treat such diseases. Lack of treatment modalities can, in part, be attributed to the lack of effective brain delivery strategies. Due to this lack of treatment methods the National Institutes of Health tumor and stroke progress review groups have even identified the search for innovative strategies for drug or gene targeting through the blood-brain barrier as a top research priority. The National Institutes of Health (NIH) guidelines instruct that such breakthroughs in basic neuroscience can be delivered to the clinic and "require an agent delivery strategy and/or the ability to target specific areas of the brain". Thus, in the absence of appropriate vehicles for targeting and trans-BBB transport, the pipeline of new CNS medicines will likely continue to be inadequate for the people suffering from neurological disorders. As examples, protein therapeutics known as neurotrophins have been investigated recently for their protective capacity in stroke, reversal of Parkinson's disease symptoms after direct infusion into the brains of human subjects, and for their ability to direct specialized differentiation of neural stem cells for potential treatment of Parkinson's disease and other neurodegenerative diseases such as Alzheimer's disease, Huntington's disease and multiple Sclerosis. Although extremely promising therapeutics, these trophic factors do not readily cross the BBB and will require a noninvasive delivery system for widespread, effective administration.

Present brain delivery strategies are particularly invasive and require circumvention of the BBB. Strategies requiring neurosurgery are used for implantation of polymer particles infused with drug, but the treatment volume is limited because the extracellular fluid in brain tissue is quiescent, and simple molecular diffusion only allows for a modest penetration distance of 2-3 mm. A similar method is direct injection of a drug into the brain ventricles, but the penetration into brain tissue is also limited for such intraventricular injections because the cerebral spinal fluid is rapidly cleared and is turned over 4-5 times daily. In addition, protein therapeutics, such as, for example, Glial-cell Line-Derived, Neurotrophic Factor (GDNF) for Parkinson's disease have been delivered through neurosurgically implanted catheters with continual drug infusion by a peripheral pump. Disruption of the BBB has been investigated using hyperosmolar solutions and vasoactive agents like serotonin and bradykinin peptides to allow free passage of molecules from the blood to the brain. This method is primarily used clinically only in terminal patients because alterations in the BBB can lead to toxic effects due to the free access of solutes and immune factors that are normally excluded from brain.

The aforementioned invasive strategies can have success for those diseases with limited treatment volumes, such as, for localized, non-metastatic brain tumors. However, for chronic conditions requiring a repetitive treatment regimen, or for those diseases present in large portions of the brain such as Alzheimer's disease, a noninvasive drug delivery strategy would be substantially more preferable and practical.

A variety of noninvasive brain drug delivery methods have been investigated that make use of the brain blood vessel network to gain widespread drug distribution. The brain capillary network has an average spacing of just 40 microns between capillaries and is sufficiently dense that each brain cell essentially has its own vessel for nutrient supply (FIG. 2). In addition, if the endothelial barrier of the BBB can be overcome such that a drug is deposited on the brain side of the BBB, the diffusion distance is short enough that each brain cell should be accessible to the drug. As a result, in contrast to invasive methods, a comprehensive treatment volume can result. These noninvasive transport systems/mechanisms can be generally clustered into three groups: 1, non-specific uptake; 2, carrier-mediated transport; and 3, receptor-mediated transport (FIG. 3).

Non-specific uptake mechanisms, while allowing some transport across the BBB, lack sensitivity and specificity. Cationic protein transduction domains fall into the realm of non-specific carriers, and although the HIV TAT peptide was shown to gain access to the brain interstitium after intraperitoneal injection, subsequent pharmacokinetic analysis indicated that the rapid clearance and broad organ uptake would necessitate very high doses to gain a pharmacologic effect. Another non-specific uptake mechanism is the surfactant coating of nanoparticles with polysorbate 80. Although the mechanism of brain uptake is still unresolved, the labile nature of the particles in vivo leads to short-lived pharmacologic effects and possible BBB permeabilization. Both of these non-specific methods suffer from a lack of selective targeting and result in widespread distribution of the active compound throughout the body with concomitant systemic effects.

Carrier-mediated drug transport relies on the presence of endogenous transmembrane proteins that are selective and stereospecific for small molecule solutes. For instance, L-dopa, administered to treat Parkinson's disease gains entry to the brain by utilizing the large amino acid transporter (LAT-1). The successful transport through the blood-brain barrier is a result of L-dopa mimicking the structure of phenylalanine with only the substitution of two hydroxyl groups on the aromatic ring of phenylalanine. Utilization of the saturable biotin transport system for delivery of biotinylated drugs has also been attempted. In addition, it is likely that the efflux of the AIDS drug AZT progresses in a carrier-mediated fashion. However, due to the stereospecificity and steric constraints imposed by these selective membrane pores, applications are potentially limited.

Receptor-mediated transport involves the binding of an exofacial epitope of a cell surface receptor and triggering of an energy intensive transcellular transport process known as transcytosis (FIG. 3). Drugs can be delivered using these portals if conjugated to the natural ligand or an antibody that can trigger the transcytosis process. This method has been successful in allowing for non-invasive transport of small molecules, proteins, genes, nanoparticles, and liposomes up to 100 nm in size. The receptors that are commonly targeted for transcytosis are the low density lipoprotein (LDL) receptor, the transferrin receptor, and the insulin receptor. Similar less specific processes involving absorptive-mediated transcytosis have been used with cationized proteins that promote receptor clustering and activation of the transcytosis pathway. Strategies oftentimes target the cell surface receptor in ways that do not disrupt the normal transport of endogenous ligand. Therefore the impact on normal metabolic pathways is limited. In addition, since transcytosis employs the vesicular trafficking system, this strategy is not nearly as limited by the size and shape constraints of carrier-mediated transport.

Antibodies are particularly well suited for targeting BBB receptor-mediated transcytosis systems given their high affinity and specificity for their ligands. As examples, appropriately-targeted antibodies that recognize extracellular epitopes of the insulin and transferrin receptors can act as artificial transporter substrates that are effectively transported across the BBB and deposited into the brain interstitium via the transendothelial route. Additionally, when conjugated to drugs or drug carriers of various size and composition, the BBB targeting antibodies mediate brain uptake of the therapeutic cargo. Noninvasive transport of small molecules such as methotrexate has been achieved using anti-transferrin receptor antibodies. Proteins such as nerve growth factor, brain derived neurotrophic factor, and basic fibroblast growth factor were delivered to the brain after intravenous administration by using an anti-transferrin receptor antibody. The latter two cases promoted reduction in stroke volume in rat middle cerebral artery occlusion models. Liposomes and liposomes containing genes have also been delivered to the brain in vivo using anti-transferrin receptor antibodies. In particular, gene-containing antibody-targeted liposomes have been targeted to rat brain for restoration of tyrosine hydroxylase activity in an experimental Parkinson's disease model and to primate brain using a humanized anti-insulin receptor antibody. In addition, brain delivery of the new class of RNA interference drugs via pegylated immunoliposomes has been demonstrated to increase survival of mice implanted with an experimental human brain tumor model. Further, anti-transferrin receptor conjugated nanoparticles have been produced. Finally, even if an antibody binds to the brain microvsculature or internalizes without full transcytosis, it can have drug delivery benefits. When conjugated to a liposome or nanoparticle loaded with lipophilic small molecule drugs, it might be possible to raise the local BBB concentration of drug and help circumvent brain efflux systems, thereby facilitating brain uptake. Finally, in the event binding occurs without transcytosis or even internalization, the identification of BBB-specific antibody receptors or ligands will further help to characterize and identify components of the transporter system and help to further optimize antibodies that do internalize and trancytose. Taken together, these results indicate the potential utility of antibody-targeted transcytosis systems for noninvasive trafficking of drugs into the brain.

Regardless of the promise shown for antibody mediated transport in prior studies, the current antibody targeting reagents lack specificity and transport efficiency. Although early results derived from the receptor-mediated transcytosis process are promising due to its robustness in delivery of drugs or drug carriers in many formats, it also has some serious drawbacks that need to be addressed for general clinical success. The present methods rely on receptors that are ubiquitously expressed like the transferrin and insulin receptors. This leads to mis-targeting of potentially expensive drugs that also may have unwanted side effects in tissues other than the brain. In addition, the present methodologies generally result in a low fraction (1-4%) of the injected dose actually reaching the brain target as a consequence of poor targeting and nonideal BBB permeability. This loss of between 96-99% of the administered therapeutic could hamper the development of these delivery approaches given the cost of drug manufacture, especially for protein and gene-based medicines that currently comprise nearly 700 drugs in various stages of clinical trials. Finally, the antibodies used in the aforementioned proof-of-concept experiments are either of murine origin or partially humanized, and this could lead to unwanted immunogenic reactions in human patients. Therefore, the identification of fully human antibodies that specifically recognize brain endothelial receptors would vastly improve the targeting and efficiency of drug delivery while minimizing side-effects.

SUMMARY OF THE INVENTION

This invention provides antibodies that bind endothelial cell receptors resulting in endocytosis of the receptor and bound ligands. In one exemplary embodiment, the invention comprises an isolated antibody fragment having the amino acid sequence set forth in any one of SEQ ID NOs. 1-34. In another embodiment, the invention provides an isolated nucleic acid having a sequence coding for an amino acid as set forth in any one of SEQ ID NOs. 1-34. In some preferred versions, the isolated antibody fragment is a single chain fragment variable (scFv) fragment. In other preferred versions, the isolated antibody is a Fab, an IgG or any other ligand specific to the endothelial cell receptor.

In another preferred embodiment, the invention is a pharmaceutical composition comprising an antibody linked to a pharmaceutically active compound that is useful in transferring the pharmaceutically active compound across the blood brain barrier (BBB).

In another exemplary embodiment, the invention is an isolated expression vector that includes a polynucleotide encoding the amino acid sequence set forth in SEQ ID NOs. 1-34. In other embodiments, the invention includes a purified and isolated host cell comprising the expression vector containing the isolated nucleic acid encoding the amino acid sequence set forth in any one of SEQ ID NOs. 1-34. It should be appreciated that the host cell can be any cell capable of expressing antibodies, such as, for example fungi, mammalian cells, including the Chinese hamster ovary cells; insect cells, using, for example, a baculovirus expression system; plant cells, such as, for example, corn, rice, *Arabidopsis*, and the like.

In yet another exemplary embodiment, the invention comprises a process for expressing an antibody fragment capable of binding to a brain endothelial cell receptor comprising: (a) displaying an antibody fragment on a yeast cell; (b) panning the antibody displaying yeast cell against a brain endothelial cell culture; (c) identifying displayed antibody fragments that specifically bind brain endothelial cell receptors; (d) inserting an isolated nucleic acid coding for the antibody fragment identified in step (c) in an expression vector; and (e) transforming a host cell with the expression vector. In some versions of this embodiment, the host cell is selected from the group consisting of: yeast, bacteria, and combinations thereof. In some preferred embodiments the host cell is *Saccharomyces cerevisiae* or *E. coli*.

In another exemplary embodiment, the invention is a method of identifying a brain endothelial cell specific antibody. This embodiment includes displaying antibody fragments on a yeast cell surface, panning the displayed antibody against a brain endothelial cell culture, isolating specific binders to the membrane receptors on the brain endothelial cell, and identifying the specific binders, thereby identifying an endothelial cell specific antibody. In some preferred embodiments the endothelial cell culture is provided in a cell monolayer.

In still another exemplary embodiment, the invention comprises a method of identifying endothelial cell receptors functioning in or related to endocytosis and transcytosis comprising, providing a cultured endothelial cell monolayer and panning a yeast-displayed antibody library against the endothelial cell monolayer, isolating antibody bound endothelial cells; and identifying the cognate receptor.

Novel human antibodies that target BBB transport systems have immense utility. Unlike the antibody delivery strategies that utilized well studied systems such as the transferrin and insulin systems, identifying novel receptor-mediated transport systems is quite difficult given that these ligands are membrane proteins that have yet to be identified. Therefore, the inventors have developed a novel selection methodology to identify fully human antibodies having the required functionality of BBB binding. The power of this technique is the concomitant selection of potential drug delivery vector and its cognate cell surface receptor (receptor-mediated carrier system) with no prior knowledge as to the origin of either component. FIG. 4 depicts a general scheme for the selection of such antibodies according to the invention.

Another aspect of the present invention is in regard to antibody targets at the blood brain barrier, particularly, targets that represent the molecular machinery for internalization (endocytosis) and transcytosis. Accordingly, the present invention is directed to a purified scFvA antigen having a molecular weight of approximately 124 kDa when immunoprecipitated by human scFvA under non-reducing conditions. The inventors identified and demonstrated this antigen is expressed in intact brain capillaries.

Accordingly, the invention further encompasses an antibody-blood brain barrier transporter system. Such a system includes: (a) an antigen having a molecular weight of approximately 124 kDa when immunoprecipitated by human scFvA under non-reducing conditions, the antigen expressed in intact brain capillaries; and (b) a purified antibody bound to the scFvA antigen. The purified antibody has the amino acid sequence set forth in any one of SEQ ID NOs:1-5, more preferably the antibody is scFvA having the amino acid sequence set forth in SEQ ID NO:1. In certain embodiments, the purified antibody is provided in combination with a pharmaceutically active compound.

Based upon the disclosed antibody-blood brain barrier transporter system, the invention also contemplates a method of delivering a pharmaceutically active compound across the blood brain barrier to a subject's brain. Such a method includes administering a pharmaceutically active compound in combination with a purified antibody having an amino acid sequence of any one of SEQ ID NOs:1-5 to a subject such that the antibody directs delivery of the pharmaceutically active compound across the blood brain barrier to the subject's brain.

These and other features and advantages of various exemplary embodiments of the articles and methods according to this invention are described in, or are apparent from, the following detailed description of various exemplary embodiments of the methods according to this invention.

BRIEF DESCRIPTION OF THE DRAWINGS

Various exemplary embodiments of the methods of this invention will be described in detail, with reference to the following figures, wherein:

FIG. 1A shows that horseradish peroxidase is sequestered in brain blood vessels and does not access the parenchyma, except for in the small circumventricular organs that lack a BBB (median eminence above). FIG. 1B. illustrates the effectiveness of the BBB: radio-labeled histamine, only 111 Da, cannot enter the brain or spinal cord of the mouse.

FIG. 6A is a phase contrast image of yeast displaying 4-4-20. FIG. 6B is a fluorescence image of yeast displaying 4-4-20 bound to fluorescein-dextran (FITC-dextran). FIG. 6C is a phase contrast image of yeast displaying irrelevant scFv, D1.3. FIG. 6D is a fluorescence image of D1.3 yeast that fails to bind FITC-dextran.

FIG. 12 is a table summarizing the binding of scFv variants. (a) Unique scFv were clustered by homology. Each class of scFv antibodies differs from all other classes by at minimum one CDR3 (20% amino acid homology). The CDR3 regions were focused upon for defining classes given the nonimmune basis for the library that limits CDR1 and CDR2 diversity and the fact that CDR3 of the VH and VL play a major role in determining binding specificity and affinity. Within a class, CDR1, CDR2, and CDR3 (≧85% amino acid homology) of VH and VL all have high homology. (b) An scFv was deemed unique by amino acid sequence and BstN1 digest pattern. (c) The germline antibody gene usage was determined by subjecting the deduced scFv amino acid sequence to IgBLAST (http://www.ncbi.nlm.hig.gov/igblast/). (d) Clones subtracted in the VHCDR2 yeast Northern blot experiments were counted in the totals of either scFvA or scFvD based on their frequency of occurrence in small scale screens, and therefore represent estimates.

FIG. 13 is a sequence alignment of scFv clones B, G, C and K that show sequence homology to clone scFv A. VH—variable heavy region; VL—variable light region; CDR—complimentarity determining region.

FIG. 14 is a sequence alignment of scFv clones D, I and H that share sequence homology. VH—variable heavy region; VL—variable light region; CDR—complimentarity determining region.

FIG. 15 is a sequence alignment of scFv clones A, C, B, G, K and F illustrating that F has a similar homology to the variable light (VL) domains but not to the variable heavy (VH) domain. VH—variable heavy region; VL—variable light region; CDR—complimentarity determining region.

FIG. 16 is a polyacrylamide gel (top panel) showing that the secreted proteins have the appropriate weight for an scFv and a table (bottom panel) summarizing the binding and internalization of scFv by RBE4 cells.

FIG. 17 is a collection of micrographs illustrating dual fluorescent staining of RBE4 binding scFv's showing specific binding and internalization of scFv A by RBE4 cells but not scFv D.

DETAILED DESCRIPTION OF THE INVENTION

Figure 1:
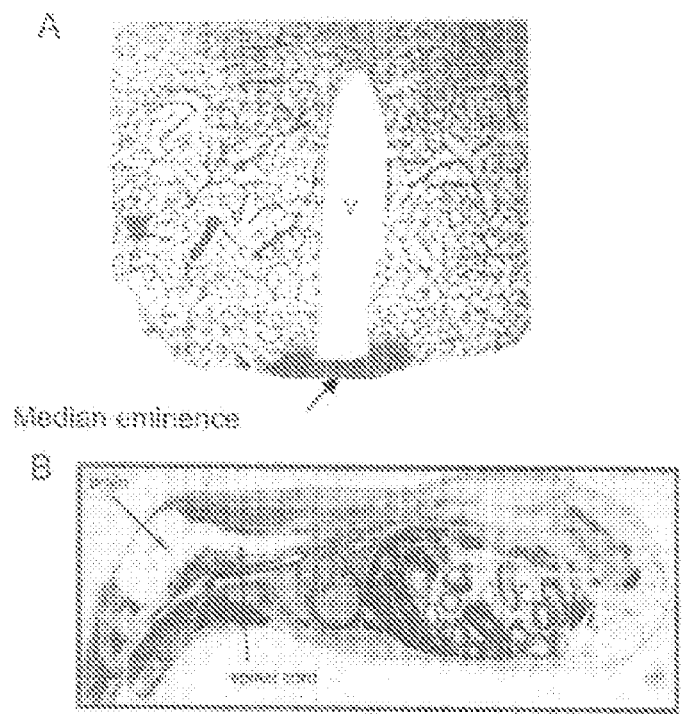
FIGS. 1A and 1B are micrographs illustrating the impermeability of the blood-brain barrier.
Figure 2:
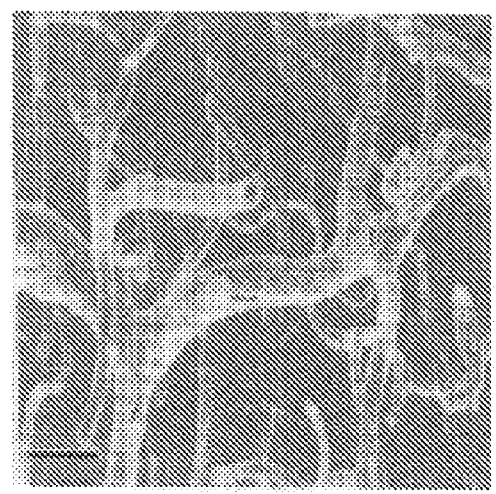
FIG. 2 is an electron micrograph of a human cerebellar cortex vascular cast illustrating the extent of the vascular network. Scale bar is 40 µm.
Figure 3:
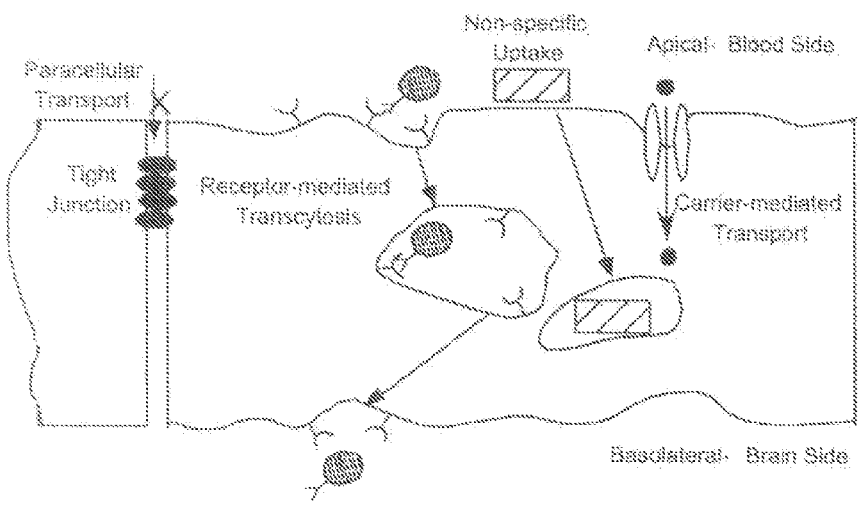
FIG. 3 is a schematic representation of various BBB transport options.

The current invention is based on the observation that cellular mechanisms may be the most efficient and effective way to transport drugs and/or therapeutics across the blood brain barrier (BBB). While a variety of cellular transporter and receptor mechanisms have been identified, they are limited by the specificity of the ligand to the endothelial receptor and by both the affinity and avidity of the ligand for the receptor. Further, identification of, as yet, unidentified antibody ligands and receptors will provide better tools by which to transport compounds across the BBB.

The inventors have mined a human single-chain antibody fragment (scFv) library for scFvs that bind to membranes of brain endothelial cells. A subset of the scFv identified as binding to brain endothelial cells also endocytose into these cells, indicating that they may be substrates for BBB transcytosis systems. The scFv also specifically labels vessels of all sizes in brain tissue sections in a pattern that represents a transport system of endothelial origin. No labeling is detected in other brain cells. This class of scFv and their associated BBB transport systems represent a novel mechanism for non-invasive drug delivery to the brain.

Before the present invention is described, it is understood that this invention is not limited to the particular methodology, protocols, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference for the purpose of describing and disclosing the chemicals, cell lines, vectors, animals, instruments, statistical analysis and methodologies which are reported in the publications which might be used in connection with the invention. Nothing herein is to be construed as an admission that the invention is not entitled to antedate such disclosure by virtue of prior invention.

As used herein "subject" means mammals and non-mammals. "Mammals" means any member of the class Mammalia including, but not limited to, humans, non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

As used herein, "administering" or "administration" includes any means for introducing compositions of the invention into the body, preferably into the systemic circulation. Examples include but are not limited to oral; buccal, sublingual, pulmonary, transdermal, transmucosal, as well as subcutaneous, intraperitoneal, intravenous, and intramuscular injection.

As used herein, "pharmaceutical composition" means therapeutically effective amounts of the BBB transcytosis compound (also termed "pharmaceutically active compound") together with suitable diluents, preservatives, solubilizers, emulsifiers, and adjuvants, collectively "pharmaceutically-acceptable carriers." As used herein, the terms "effective amount" and "therapeutically effective amount" refer to the quantity of active therapeutic agent or agents sufficient to yield a desired therapeutic response without undue adverse side effects such as toxicity, irritation, or allergic response. The specific "effective amount" will, obviously, vary with such factors as the particular condition being treated, the physical condition of the subject, the type of animal being treated, the duration of the treatment, the nature of concurrent therapy (if any), and the specific formulations employed and the structure of the compounds or its derivatives. In this case, an amount would be deemed therapeutically effective if it resulted in one or more of the following: (a) the prevention of a neurological or brain disease (e.g., Alzheimers, Parkinson's and/or cancer); and (b) the reversal or stabilization of a neurological or brain disease (e.g., Alzheimers, Parkinson's and/or cancer). The optimum effective amounts can be readily determined by one of ordinary skill in the art using routine experimentation.

Pharmaceutical compositions are liquids or lyophilized or otherwise dried formulations and include diluents of various buffer content (e.g., Tris-HCl, acetate, phosphate), pH and ionic strength, additives such as albumin or gelatin to prevent absorption to surfaces, detergents (e.g., Tween 20, Tween 80, Pluronic F68, bile acid salts), solubilizing agents (e.g., glycerol, polyethylene glycerol), anti-oxidants (e.g., ascorbic acid, sodium metabisulfite), preservatives (e.g., Thimerosal, benzyl alcohol, parabens), bulking substances or tonicity modifiers (e.g., lactose, mannitol), covalent attachment of polymers such as polyethylene glycol to the protein, complexation with metal ions, or incorporation of the material into or onto particulate preparations of polymeric compounds such as polylactic acid, polyglycolic acid, hydrogels, etc, or onto liposomes, microemulsions, micelles, milamellar or multilamellar vesicles, erythrocyte ghosts, or spheroplasts. Such compositions will influence the physical state, solubility, stability, rate of in vivo release, and rate of in vivo clearance. Controlled or sustained release compositions include formulation in lipophilic depots (e.g., fatty acids, waxes, oils).

Further, as used herein "pharmaceutically acceptable carriers" are well known to those skilled in the art and include, but are not limited to, 0.01-0.1M and preferably 0.05M phosphate buffer or 0.9% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media.

For purposes of the present invention, "treating" or "treatment" describes the management and care of a subject for the purpose of combating the disease, condition, or disorder. The terms embrace both preventive, i.e., prophylactic, and palliative treatment as well as therapeutic treatment. Treating includes the administration of a compound of present invention to prevent the onset of the symptoms or complications, alleviating the symptoms or complications, or eliminating the disease, condition, or disorder.

In one exemplary embodiment, the invention comprises an isolated antibody fragment having the amino acid sequence set forth in any one of SEQ ID NOs. 1-34. In some preferred versions, the isolated antibody fragment is a single chain fragment variable (scFv) fragment.

In another exemplary embodiment, the invention provides antibodies that bind endothelial cell receptors resulting in endocytosis of the receptor and bound ligands. In some embodiments, the invention is a pharmaceutical composition comprising an antibody linked to a pharmaceutically active compound that is useful in transferring the pharmaceutically active compound across the blood brain barrier (BBB).

In another exemplary embodiment, the invention is an expression vector that includes a polynucleotide encoding the amino acid sequence set forth in any one of SEQ ID NOs. 1-34. In other embodiments, the invention includes a purified and isolated host cell comprising the expression vector containing the isolated nucleic acid encoding the amino acid sequence set forth in any one of SEQ ID NOs. 1-34. It should be appreciated that the host cell can be any cell capable of expressing antibodies, such as, for example fungi, mammalian cells, including the Chinese hamster ovary cells; insect cells, using, for example, a baculovirus expression system; plant cells, such as, for example, corn, rice, Arabidopsis, and the like. See, generally, Verma, R. et al., *J Immunol Methods*. 1998 Jul. 1; 216(1-2):165-81.

In yet another exemplary embodiment, the invention comprises a process for expressing an antibody fragment capable of binding to a brain endothelial cell receptor comprising: (a) displaying an antibody fragment on a yeast cell; (b) panning the antibody-displaying yeast cell against a brain endothelial cell culture; (c) identifying displayed antibody fragments that specifically bind brain endothelial cell receptors; (d) inserting an isolated nucleic acid coding for the antibody fragment identified in (c) in an expression vector; and (e) transforming a host cell with the expression vector. In some versions of this embodiment, the host cell is selected from the group consisting of: yeast, bacteria, and combinations thereof. In some preferred embodiments the host cell is *Saccharomyces cerevisiae* or *E. coli*.

In another exemplary embodiment, the invention is a method of identifying a brain endothelial cell specific antibody. This embodiment includes displaying antibody fragments on a yeast cell surface, panning the displayed antibody against a brain endothelial cell culture, isolating specific binders to the membrane receptors on the brain endothelial cell, and identifying the specific binders, thereby identifying an endothelial cell specific antibody. In some preferred embodiments the endothelial cell culture is provided in a cell monolayer.

In still another exemplary embodiment, the invention comprises a method of identifying endothelial cell receptors functioning in or related to endocytosis and transcytosis comprising, providing a cultured endothelial cell monolayer and panning a yeast-displayed antibody library against the endothelial cell monolayer, isolating antibody bound endothelial cells; and identifying the cognate receptor.

Figure 4:
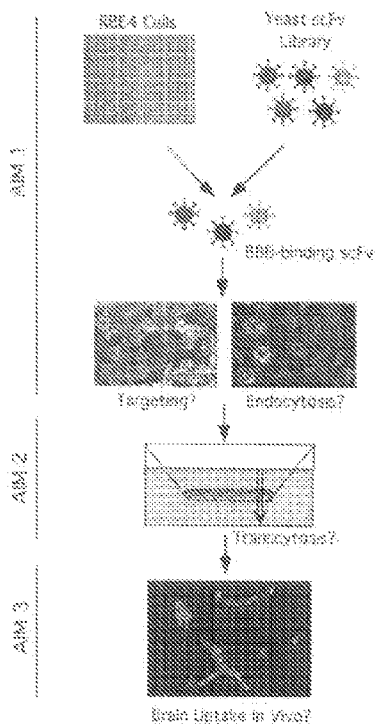
FIG. 4 is a flowchart of one embodiment of antibody-mediated brain endothelial cell transcytosis.

Novel human antibodies that target BBB transport systems have immense utility. Unlike the antibody delivery strategies that utilized well studied systems such as the transferrin and insulin systems, identifying novel receptor-mediated transport systems is quite difficult given that these ligands are membrane proteins that have yet to be identified. Therefore, the inventors have developed a novel selection methodology to identify fully human antibodies having the required functionality of BBB binding. The power of this technique is the concomitant selection of potential drug delivery vector and its cognate cell surface receptor (receptor-mediated carrier system) with no prior knowledge as to the identity of either component. FIG. 4 depicts a general scheme for the selection of such antibodies according to the invention.

If antibodies are used to target receptor-mediated transport systems at the BBB, then drug molecules and drug carriers can be effectively transcytosed across the BBB endothelium into brain tissue. Such noninvasive delivery from blood to brain is a result of the antibody acting as a surrogate ligand for the endogenous transport systems. Current known antibody-targeted brain delivery systems include the transferrin and insulin receptor systems. These receptors are expressed ubiquitously throughout the body and lead to mistargeting of expensive pharmaceuticals.

Depending on the neuronal disorder targeted, a variety of brain drug cargoes, e.g. pharmacologic compounds or, equivalently, pharmaceutically active compounds, can be delivered successfully in vivo using antibody-based targeting according to the invention. As used herein, the terms "pharmaceutically active compound" and "pharmacologic compound" shall refer to any compound useful in treating or ameliorating the effects of a disease or disorder. For example, diseases including neurodegenerative diseases such as Alzheimer's disease, Parkinson's disease, Huntington's disease, amyotrophic lateral sclerosis (ALS, Lou Gehrig's disease) and multiple sclerosis can be targeted by use of such drugs as neurotrophic factors, including, but not limited to, nerve growth factor (NGF), brain derived neurotrophic factor (BDNF), ciliary neurotrophic factor (CNTF), glial cell-line neurotrophic factor (GDNF) and insulin-like growth factor (IGF). In addition, other compounds that have been shown to have therapeutic potential and may be delivered by antibodies of the invention are neuropeptides, including, but not limited to, Substance P, neuropeptide Y, vasoactive intestinal peptide (VIP), gamma-amino-butyric acid (GABA), dopamine, cholecystokinin (CCK), endorphins, enkephalins and thyrotropin releasing hormone (TRH). Further, therapeutics may include cytokines, anxiolytic agents, anticonvulsants, polynucleotides and transgenes, including, for example, small-interfering RNAs which may be used for such neuronal disorders, including, but not limited to, psychiatric illnesses, such as, for example anxiety, depression, schizophrenia, and sleep disorders, as well as epilepsies, seizure disorders, stroke and cerebrovascular disorders, encephalitis and meningitis, memory and cognition disorders, pain therapeutics and physical trauma.

Antibodies are particularly well suited for targeting BBB receptor-mediated transcytosis systems given their high affinity and specificity for their ligands. As examples, appropriately-targeted antibodies that recognize extracellular epitopes of the insulin and transferrin receptors can act as artificial transporter substrates that are effectively transported across the BBB and deposited into the brain interstitium via the transendothelial route. Additionally, when conjugated to drugs or drug carriers of various size and composition, the BBB targeting antibodies mediate brain uptake of the therapeutic cargo. Noninvasive transport of small molecules such as methotrexate has been achieved using anti-transferrin receptor antibodies. Proteins such as nerve growth factor, brain derived neurotrophic factor, and basic fibroblast growth factor were delivered to the brain after intravenous administration by using an anti-transferrin receptor antibody. The latter two cases promoted reduction in stroke volume in rat middle cerebral artery occlusion models. Liposomes and liposomes containing genes have also been delivered to the brain in vivo using anti-transferrin receptor antibodies. In particular, gene-containing antibody-targeted liposomes have been targeted to rat brain for restoration of tyrosine hydroxylase activity in an experimental Parkinson's disease model and to primate brain using a humanized anti-insulin receptor antibody. In addition, brain delivery of the new class of RNA interference drugs via pegylated immunoliposomes has been demonstrated to increase survival of mice implanted with an experimental human brain tumor model. In addition, anti-transferrin receptor conjugated nanoparticles have been produced. Finally, even if an antibody binds to the brain microvasculature or internalizes without full transcytosis, it can have drug delivery benefits. When conjugated to a liposome or nanoparticle loaded with lipophilic small molecule drugs, it might be possible to raise the local BBB concentration of drug and help circumvent brain efflux systems, therefore facilitating brain uptake. Further, the ability to bind without internalization or with internalization but without full trancytosis will provide for the identification of BBB endothelial receptors or ligands that, once known, will allow for characterization and identification of the transporter system and for optimization of antibodies that are internalized and/or trancytosed. Taken together, these results indicate the utility of antibody-targeted transcytosis systems for noninvasive trafficking of drugs into the brain.

As can be appreciated, one aspect of the present invention is in regard to antibody targets at the blood brain barrier, particularly, targets that represent the molecular machinery for internalization (endocytosis) and transcytosis. Accordingly, the present invention is directed to a purified antigen having a molecular weight of approximately 124 kDa when immunoprecipitated by human scFvA under non-reducing conditions. The inventors identified and demonstrated this antigen is expressed in intact brain capillaries. The inventors have further demonstrated that scFvB, scFvC, scFvG, and scFvK each recognize and are capable of immunoprecipitating the approximately 124 kDa antigen immunoprecipitated by scFvA. Accordingly, scFvA, scFvB, scFvC, scFvG, and scFvK (SEQ ID NOs:1-5, respectively) are each useful as inventive blood brain targeting antibodies.

Accordingly, the invention further encompasses an antibody-blood brain barrier transporter system. Such a system includes: (a) an antigen having a molecular weight of approximately 124 kDa when immunoprecipitated by human scFvA under non-reducing conditions, the antigen expressed in intact brain capillaries; and (b) a purified antibody bound to the antigen wherein said antibody has the amino acid sequence set forth in any one of SEQ ID NOs:1-5. The purified antibody is preferably an scFvA antibody (SEQ ID NO:1), and, even more preferably, the scFvA antibody is provided in combination with a pharmaceutically active compound.

Based upon the disclosed antibody-blood brain barrier transporter system, the invention also contemplates a method of delivering a pharmaceutically active compound across the blood brain barrier to a subject's brain. Such a method includes administering a pharmaceutically active compound in combination with a purified antibody having an amino acid sequence set forth in any one SEQ ID NOs:1-5 to a subject such that the antibody directs delivery of the pharmaceutically active compound across the blood brain barrier to the subject's brain. The purified antibody is preferably an scFvA antibody having the amino acid sequence set forth in SEQ ID NO:1.

In general, methods of conjugating, linking and coupling antibodies to pharmacologically active compounds are well known in the field. For example, see Wu A M, Senter P D, Arming antibodies: prospects and challenges for immunoconjugates, *Nat. Biotechnol.* 2005 Sep.; 23(9):1137-46 and Trail P A, King H D, Dubowchik G M, Monoclonal antibody drug immunoconjugates for targeted treatment of cancer, *Cancer Immunol Immunother.* 2003 May; 52(5):328-37; Saito G, Swanson J A, Lee K D. Drug delivery strategy utilizing conjugation via reversible disulfide linkages: role and site of cellular reducing activities, *Adv Drug Deliv Rev.* 2003 Feb. 10; 55(2): 199-215. As well, the present antibodies may be provided in combination with liposome, nanoparticles or other analogous carriers loaded with a pharmaceutically active compound. Methods of preparing such compositions are known in the field (see, for example, Sugano et al., Antibody Targeting of Doxorubicin-loaded Liposomes Suppresses the Growth and Metastatic Spread of Established Human Lung Tumor Xenografts in Severe Combined Immunodeficient Mice *Cancer Research* 60, 6942-6949, Dec. 15, 2000 and Martin et al., Nanomaterials in Analytical Chemistry, *Analytical Chemistry News & Features*, May 1, 1998; pp. 322 A-327 A). As used herein, the phrase "antibody in combination with a pharmaceutically active compound" shall not be limited by the method of manufacture and such compositions may be produced by, but not limited to, techniques of conjugating, linking, coupling and decorating known in the art.

The examples described below disclose antibody delivery vectors that are a critical component for disease-based applications. Identification of such vectors combines an innovative combinatorial antibody screening technology with expertise in the BBB and brain drug delivery fields to attack a complex delivery problem.

EXAMPLES

Various exemplary embodiments of compounds obtained as generally described above and methods according to this invention will be understood more readily by reference to the following examples, which are provided by way of illustration and are not intended to be limiting of the invention in any fashion.

Example 1

In Vitro Profiling of Brain Endothelial Cell Surface Using Large ScFv Libraries

Figure 5:
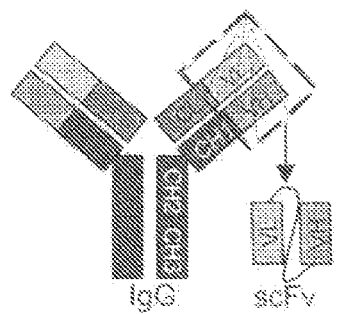
FIG. 5 is a cartoon of an immunoglobulin molecule illustrating the position of the variable regions and the origin of the single-chain antibody variable fragment (scFv). Variable light and heavy regions are connected by a flexible polypeptide linker and comprise the minimal binding subunit of an intact antibody.
Figure 6:
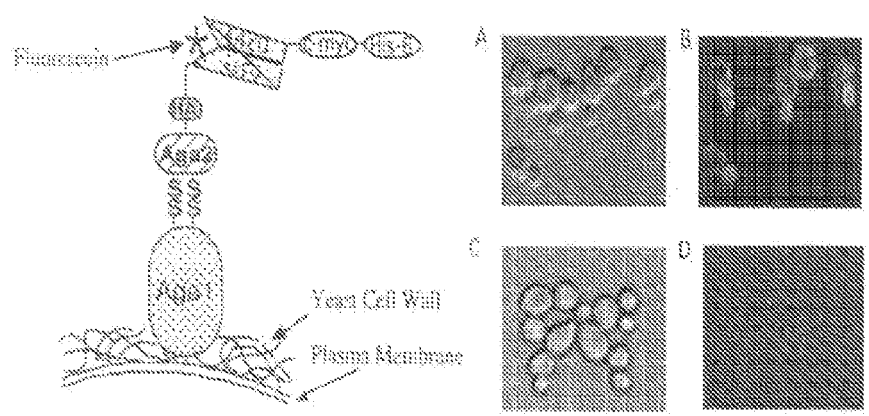
FIGS. 6A-D are schematic representations of yeast surface display of an scFv construct (4-4-20) whose antigen is fluorescein. The scFv protein is fused to the self-assembling, mating agglutinin proteins (Aga1p and Aga2p) allowing surface display of scFv proteins that actively bind fluorescein on the surface of the yeast particle.

In order to simultaneously identify both brain endothelial cell surface proteins (potential BBB-resident transport systems) and antibody targeting reagents (drug delivery vector), the inventors have performed validation of a novel cell surface profiling or "panning" technique. This technique uses a combinatorial library of naïve single-chain antibodies (scFv, FIG. 5) displayed on the surface of yeast to probe the surface of endothelial cells. The antibody library contains ~$10^9$ different scFv, and this diverse collection can be thought of as an "in vitro immune system". In this context, antibody-cell surface antigen pairs can be identified in a high throughput fashion. Yeast surface display has been well established as a technology for the directed evolution of antibody and T-cell receptors. The display system involves tethering single-chain antibodies to endogenous yeast mating agglutinins via a polypeptide linker (FIG. 6). This platform results in the display of $10^4$-$10^5$ copies of a given scFv on the yeast cell surface where it is in prime position to sample the extracellular environment. Once a single yeast clone is isolated from a library of antibodies, it acts as a "monoclonal" scFv producer. For the profiling of the endothelial cell surface targeting efficacy, experiments were performed on model ligand systems confirming that it is possible to perform yeast cell-endothelial cell screens. Similar screens were then performed to identify scFvs recognizing endocytosing brain endothelial cell surface constituents.

Example 2

Yeast Cell-Endothelial Cell Targeting with a Model Ligand

The effectiveness of the panning method was first investigated using a model scFv-surface ligand system (Wang, X. X.

and Shusta, E. V. The use of scFv-displaying yeast in mammalian cell surface selections. J Immunol Methods 2005, 304, 30-42) (incorporated herein in its entirety for all purposes). Briefly, the hapten fluorescein was used as the surface ligand and an anti-fluorescein scFv (4-4-20) was used as the yeast-displayed antibody. This system allowed detailed investigation of the factors governing panning success. Yeast displaying 4-4-20 exhibited specific interactions with fluoresceinated rat brain endothelial cells (RBE4 cell line Roux, F., et al., Regulation of gamma-glutamyl transpeptidase and alkaline phosphatase activities in immortalized rat brain microvessel endothelial cells. J Cell Physiol 1994, 159, 101-13.) (FIG. 7) and could be recovered from large backgrounds of nonbinding irrelevant yeast (1 in $10^6$) in just three rounds. These high efficiency selections required as few as 1700 fluorescein ligands per cell indicating the sensitivity and applicability to low abundance membrane proteins (transporters). Addition of free fluorescein competitor was able to completely ablate the yeast-EC interactions, confirming the specificity of the interaction.

Figure 7:
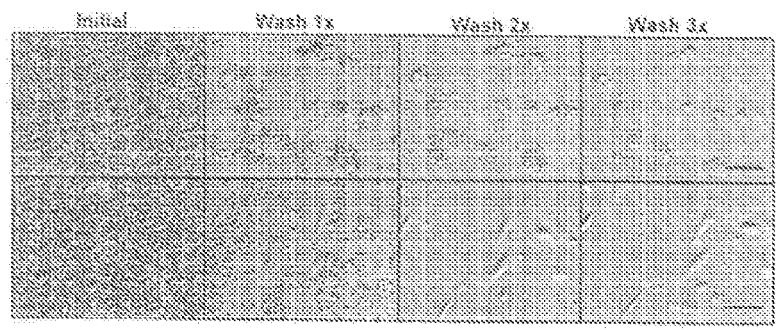
FIG. 7 is a phase contrast image showing the specific interaction between yeast displaying 4-4-20 scFv and FITC-labeled RBE4 cells. Conjugation of 4-4-20 yeast cells with biotinylated and neutravidin-FITC (NAFITC) labeled (top row) or unlabeled (bottom row) RBE4 cells. Yeast and RBE4 cells can be distinguished by their size, 4 μm and 20 μm respectively. Images of the same microscope fields were taken before and after each washing step. Scale bar: 50 μm. As shown, the FITC labeled cells exhibit continued binding to yeast after 3 washes while the non-FITC labeled cells do not.
Figure 8:
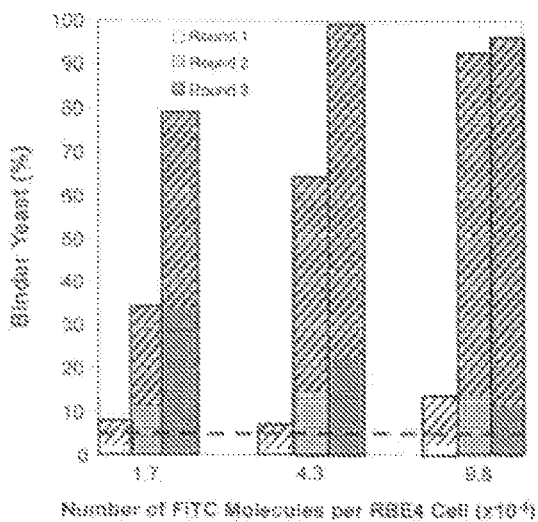
FIG. 8 is a bar graph showing the effects of scFv affinity on multiple round enrichment. Mixtures containing 4-4-20, 4M5.3 and D1.3 yeast (1:1:1×10$^5$) were panned against NAFITC-labeled RBE4 cell monolayers. After each round, the fractions of 4-4-20 and 4M5.3 in the mixture were evaluated by flow cytometry. Solid bars correspond to 4-4-20 percentage and hatched bars correspond to 4M5.3 percentage. The dotted line indicates the detection limit of the flow cytometry assay.

The effects of scFv affinity on conjugate formation were examined since the naïve yeast library contains antibodies with affinities in the nanomolar range. The extent of enrichment was analyzed for dilute mixtures containing both 4-42-0 (Kd=1.3 nM) and a high affinity mutant 4M5.3 (Kd=270 fM) [55] at varying cell surface FITC intensities. Briefly, 4-4-20: 4M5.3:nonbinder mixtures of $1:1:10^5$ were applied to NAFITC-labeled monolayers having varying densities of fluorescein ligand. After a two hour incubation at 4° C., the wells were washed to remove non-specific binders. The simultaneous enrichment of 4-4-20 and 4M5.3 was analyzed over three consecutive enrichment rounds (FIG. 7). At 1,700 ligands per cell, both scFvs enriched with nearly equal efficiencies, while at the intermediate ligand densities, the 4M5.3 enriched more rapidly. In these cases, the final product after three rounds contained between 15-25% 4-4-20 with the balance being the higher affinity 4M5.3 scFv (FIG. 8). This result shows that it is possible to extract multiple scFv clones against a single cell surface target and also suggests that scFvs against multiple antigens can be simultaneously enriched using this method. Therefore, the next step was to complete a panning selection against true endothelial antigens. An initial strategy for cell culture panning of a yeast display library was developed as shown in FIG. 9.

Example 3

Figure 9:
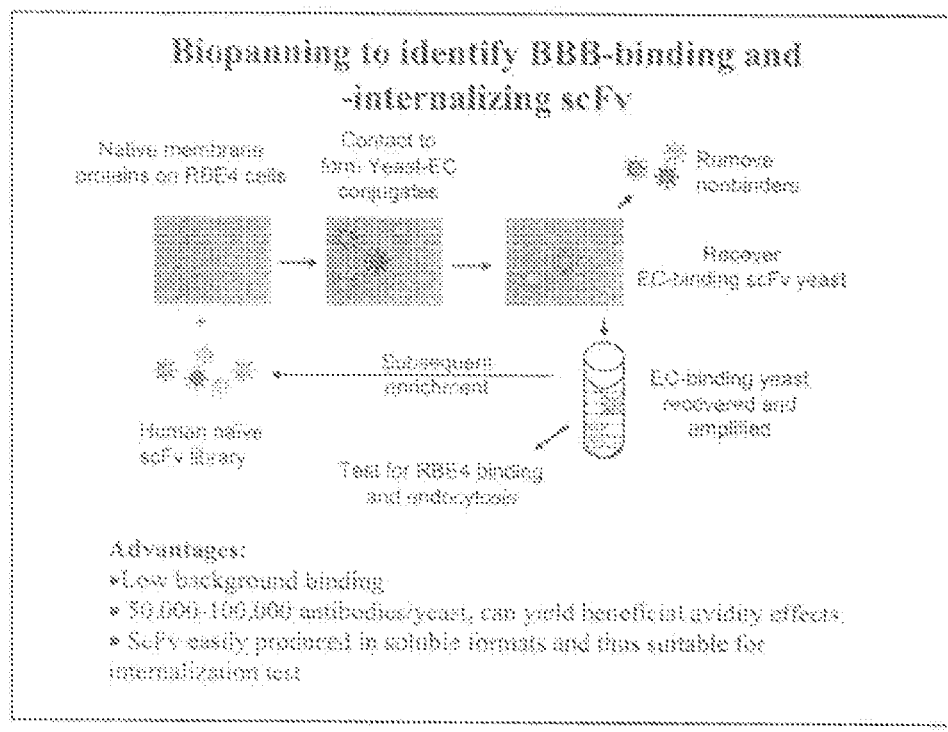
FIG. 9 is a schematic representation illustrating the overall strategy of biopanning to identify BBB-binding and internalizing scFv.

Overall Strategy for Identification of Blood Brain Barrier—Binding and Internalizing scFv Recognizing the limitations of phage-display, the strategy illustrated in FIG. 9 was developed as a more powerful assay for the identification of scFv's that bind brain endothelial cells. Briefly, as schematically represented in FIG. 9, the scFv library was mixed with an in vitro culture of brain endothelial cells. If a yeast cell has an antibody against a surface protein on endothelial cells, the yeast cell can bind to endothelial cells under proper conditions. If the surface protein is at a higher level, the binding may be more robust. This allowed the yeast binders to be recovered to perform further binding and purification. Specific binders were subjected to functionality tests to determine if they can be endocytosed and trancytosed by endothelial cells and to further identify brain-epitope specificity. This is the first example of yeast-display antibody screening on whole cells. There are numerous advantages to performing antibody screening using yeast-display (YSD) instead of phage-display. YSD has a very low background binding, due to the flocculin-deficient strain of yeast expressing the scFv library; in contrast, phage particles tend to non-specifically bind to mammalian target cells thereby giving false-positive binders. In addition the low background in YSD increases the signal to noise ratio thereby leading to fast enrichment of binding clones and also the ability to identify clones that bind with low affinity. Yeast express from 50,000 to 100,000 scFv on their surface while phage display antibody libraries express only 0-5 Ab/phage. This large number of expressed surface scFv's allows for further identification of weak binders due to the avidity effect which could cause strong cumulative interactions between relatively low affinity Abs and their antigens. Further, scFv displayed on yeast surface can be easily produced as a soluble protein by shuttling the scFv expression cassette into a secretion-expression vector. Thus, internalization studies of the scFv can be performed.

Example 4

Figure 10:
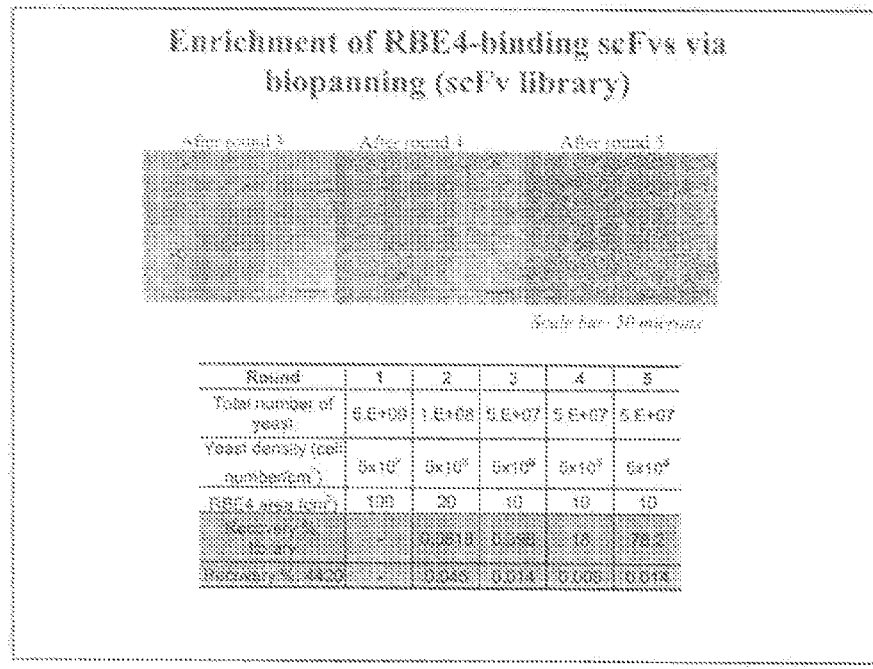
FIG. 10 illustrates the enrichment of RBE4-binding scFv's via biopanning.

Successful Screening of Human Nonimmune scFv Library for Brain Endothelial Cell Binding Clones The inventors possess a human nonimmune scFv library in the identical yeast display format as that used for the studies described in Example 1. Methods of making such a library are known in the art and have been described by, e.g., Feldhaus et al. at *Nat. Biotechnol.* 21(2):163-70 (2003), incorporated by reference herein. The library is comprised of $\sim 1 \times 10^9$ scFvs that represent much of the in vivo human antibody heavy and light chain gene diversity. Since the library is naïve, it has not been subjected to any prescreening against antigen and thus can provide antibodies that bind a widely diverse range of antigens. The library has been successfully used to isolate panels of scFvs that bind with high affinity ($K_d$=1-1000 nM) to hapten antigens (fluorescein), peptide antigens having different phosphorylation states (p53), protein antigens (lysozyme), and the extracellular portion of cell surface receptors (epidermal growth factor receptor). The yeast-EC targeting method described in Example I was used for the profiling of RBE4 rat brain endothelial cells using the scFv library. Briefly, the yeast library was applied to 100 cm² of RBE4 cells, and the binding yeast clones recovered and amplified (FIG. 9). This process was repeated for three more rounds on 20, 10, and 10 cm² of RBE4 cells, respectively. The surface area of endothelial cells required decreases progressively with each round since the diversity of the library decreases. Thus, fewer yeast clones need to be examined to exhaustively cover the enriched pools. After just four rounds of selection, the number of recovered yeast was nearly equal to the number of yeast applied to the RBE4 cells indicating that almost the entire pool was comprised of endothelial cell binding yeast clones (FIG. 10). Next, the individual clones from the recovered yeast pool were analyzed on a high throughput basis to determine the identity of the scFvs mediating yeast-RBE4 cell binding.

Example 5

Efficacy of Identification and Enrichment of RBE4-Binding scFv's via Biopanning

The inventors developed the biopanning antibody library screening method based on the model system described in EXAMPLE 2. This model was then applied to the YSD scFv library to identify BBB-binding and internalizing antibodies. Preparation of the library is described by Wang et al. at *Nat.*

*Methods*, 4(2):143-5 (2007) which, along with the references cited therein, is incorporated by reference into the present disclosure. FIG. 10 illustrates the effects of multiple rounds of enrichment using this method. As shown, after 4 rounds of panning, there were a lot of yeast cells retained by the RBE4 cells compared to after the third round. Further, almost all of the input yeast population was recovered after the fifth round indicating that four rounds of screening is apparently enough to "pull out" the BBB binders and the presubtraction experiments against other cell types or endothelium could be used to screen for brain specificity. The recovery percentage of the library is listed in the table in the lower panel of FIG. 10. The efficacy of the method is illustrated by the increasing recovery percentage of the library after progressive panning rounds. In comparison, the values for the negative control 4-4-20 yeast stayed the same.

Example 6

High Throughput Analysis of RBE4 Binding Competent Yeast Clones

Figure 11:
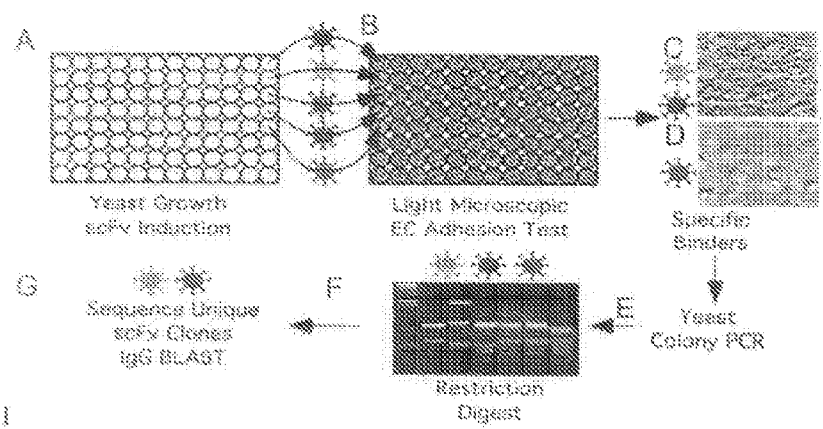
FIG. 11 is a schematic diagram of the cell monolayer panning and high throughput yeast clone profiling strategy. 11A, yeast growth in 96-well plate; 11B, yeast are added to RBE4 culture; 11C, induced yeast; 11D, non-induced; 11E initial PCR or binders; 11F Restriction digest providing "fingerprint" of binders and identifying germline family; 11G sequencing of unique scFv clones.

While the capability of the inventors' panning system was illustrated by the results shown in FIG. 10, the inventors still needed a method by which to rapidly review the clones in the library. Therefore, the inventors developed a method to allow the high-throughput screening and sequencing of binding clones. Briefly, yeast clones were grown in a 96-well format such that scFv expression was induced on their surface (FIG. 11A). The yeast were then transferred directly to a 96-well plate containing RBE4 cell monolayers (FIG. 11B). Subsequent to appropriate washing, the 96-well plate was scanned by light microscopy. Yeast clones that truly mediate binding are simply identified by the retention of yeast on the RBE4 cell monolayer (FIG. 11C). To ensure that endothelial cell binding is not simply a result of a spurious genetic mutation in the yeast strain, a parallel plate was tested using yeast grown in a carbon source that does not allow induction of scFv expression (FIG. 11D). After incubation and washing steps, the induced binder clones (FIG. 11C) had many yeast left but there were relatively few for the noninduced yeast (FIG. 11D). The nonbinder clones had few yeast left for both induced and noninduced groups. No yeast mutants were identified in this particular screen and all binding was scFv mediated. Once the yeast binders were identified, colony PCR was performed to amplify the open reading frame of each scFv clone (FIG. 11E). Briefly, the scFv-encoding plasmid was amplified directly from the yeast cells using restriction enzyme BstNI. This enzyme cuts DNA frequently so different DNA would show different digestion patterns or fingerprints (FIG. 11F). Unique scFv clones will generally exhibit a different restriction profile due to the frequent occurrences of the five nucleotide BstNI recognition site. ScFvs having unique BstNI digestions were subject to sequencing. The PCR product of each clone exhibiting a unique restriction pattern was directly sequenced and the germline origin identified by IgG-BLAST (FIG. 11G). A summary of unique clones is provided in the table shown in FIG. 12.

Example 7

Summary of Binding scFv Variants

FIG. 12 is a table summarizing binding of scFv variants. As shown, to date, a total of 2000 clones have been screened. Of the 2000 clones, 1760 bound RBE4 cells. The binding clones are listed in FIG. 12. The clones are organized such that the scFv's of the same germline usages are clustered together. scFv's in each subset share high sequence homology. However, regardless of the homology, CDRs varying in only 1 amino acid may bind different antigens and thus, each may be unique binders. Further, even if the clones bound the same antigen they may bind with different affinity. In addition, it should be noted that some of the scFv's appear only once among all the clones screened. This illustrates the power of the high throughput screening method developed as such rare binders would otherwise not have been detected.

Example 8

Identification of scFv Germline Family

The germline family usages of these clones are summarized in FIG. 12. Unique scFv were clustered by homology. Each class of scFv antibodies differs from all other classes by at minimum one CDR3 (<20% amino acid homology). The CDR3 regions were focused upon for defining classes given the nonimmune basis for the library that limits CDR1 and CDR2 diversity and the fact that CDR3 of the VH and VL play a major role in determining binding specificity and affinity. Within a class, CDR1, CDR2 and CDR3 (>85% amino acid homology) of VH and VL all have high homology. FIG. 12 also shows that scFv A and D dominate in the analyzed clones. This would prevent the analysis of more clones so the inventors developed an in situ Northern blotting method to first identify scFv A and D and then analyze non-A or D clones using the high-throughput method.

A total of approximately 2000 clones from the fourth round of panning have been analyzed using this method. Of the 34 unique scFvs identified thus far, only a few clones were recovered multiple times, and based on statistical considerations, many unique clones remain in the enriched round 4 pool. The germline origins of the heavy and light variable regions for the recovered clones are indicated in FIG. 12 and two clones (E and J) consist only of the heavy chain variable region. The complete method allows for rapid analysis of 1000's of BBB binding scFv clones. A sequence alignment of the scFv A-like clones is given in FIG. 13, an alignment of the scFv D-like clones is given in FIG. 14 and an alignment of F with the A-like clones is given in FIG. 15.

Example 9

Binding and Internalization of scFv by RBE4

While the test for efficacy of the yeast library began with an identification of the binding clones, their use in transcytosis further requires that the scFvs could be internalized. Therefore, the scFv's were also examined to see if they could be internalized by RBE4 cells. Because yeast are too big to be internalized the scFv was produced as a soluble protein in yeast cell culture. To do this, scFv gene in the YSD plasmid was subcloned into a secretion plasmid (described below in EXAMPLE 10) and the scFv was then secreted into the yeast cell culture medium. Briefly, the scFv open reading frames for several of the scFvs in FIG. 12 were subcloned into a yeast expression system that yields mg/L levels of active, purified scFv (Shusta, E. V., et al., Directed evolution of a stable scaffold for T-cell receptor engineering. Nat Biotechnol 2000, 18, 754-9; Shusta, E. V., et al., Increasing the secretory capacity of *Saccharomyces cerevisiae* for production of single-chain antibody fragments. Nat Biotechnol 1998, 16, 773-7; Shusta, E. V., et al., Yeast polypeptide fusion surface display levels predict thermal stability and soluble secretion efficiency. J Mol Biol 1999, 292, 949-56). This system is regulated by the galactose-inducible GAL1-10 promoter and includes c-terminal c-myc epitope and a six histidine epitope tag for purification.

FIG. 16 shows the results of running the soluble scFv's on polyacrylamide gels (top panel), all exhibiting an appropriate size for scFv's ranging from 28-35 kDs with expression levels ranging from 1-4 mg/ml. As shown in FIG. 17, when the RBE4 cells were labeled with these soluble scFvs, the A-group showed strong labeling of RBE4 cells and could also be internalized. On the other hand, the D-group scFvs and scFvF showed binding to RBE4 cells but were not internalized. The results of these experiments are summarized in the bottom panel of FIG. 16 and below.

Figure 20:
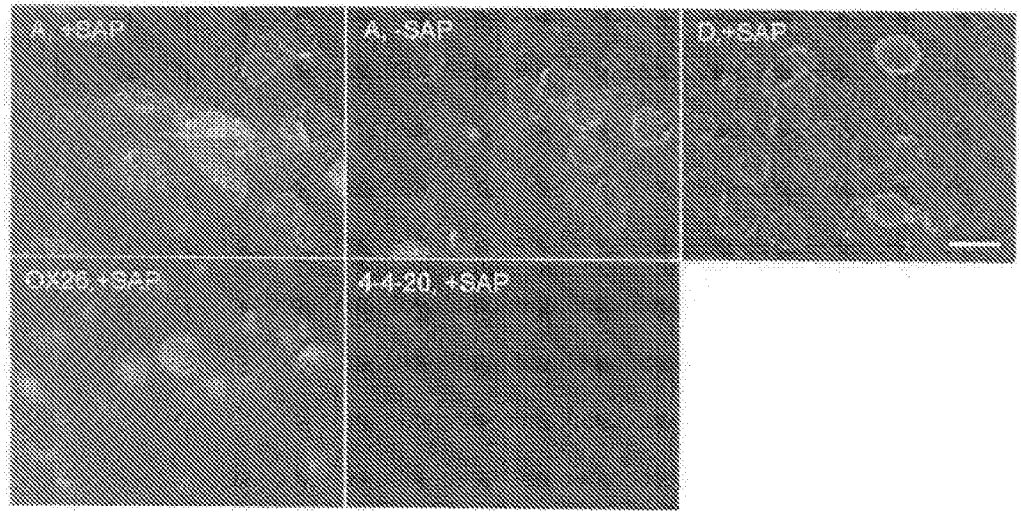
FIG. 20 are fluorescence micrographs allowing evaluation of scFv binding and internalization properties. RBE4 cells were labeled with purified, pre-dimerized scFvA, scFvD, irrelevant scFv 4-4-20 or OX26 monoclonal antibody at 4° C. for cell surface labeling and then shifted to 37° C. to promote cellular trafficking. The cells were then labeled with AlexaFluor 555 conjugated anti-mouse IgG at 4° C. followed by AlexaFluor 488 conjugated anti-mouse IgG with or without cell permeabilization by saponin (SAP) treatment. Merged images of the AlexaFluor-labeled images are shown. Scale bar: 20 μm.

Several of the class 1, 2, and 3 scFv were evaluated for their ability to mediate cellular internalization. The scFv were predimerized with the anti-cmyc epitope tag antibody to provide the bivalency often required for receptor clustering and endocytosis. The dimerized scFv were then applied to living RBE4 cells at 4° C. to yield cell surface labeling. Subsequently, the RBE4 cells were shifted to 37° C. for 30 minutes to enable cellular trafficking (FIGS. 17 and 20). Class 1 scFvA was rapidly internalized into vesicular structures within the RBE4 cells, whereas class 2 scFvD and class 3 scFvF bound the RBE4 surface but did not promote internalization. Control anti-fluorescein antibody (4-4-20) exhibited no binding or uptake. As suggested by the distinct internalization patterns, scFvA and OX26 do not compete for the same transport system. In addition, the transporter-scFvA interaction is not sensitive to glycosylation status as deglycosylation of RBE4 cells (mannosidase and neuraminidase) prior to binding and internalization had no observable effect. Further, the high homology of the scFvA clones B, C, G and K, shown in FIG. 12, indicates that members of this family may be equally effective in promoting internalization.

More specifically, RBE4 cells were labeled with predimerized scFv A, scFv D, scFv 4-4-20 (dimerized to promote receptor clustering often required for endocytosis) or OX26 monoclonal antibody at 4° C. for cell surface labeling and then shifted to 37° C. to promote cellular trafficking. The cells were then labeled with AlexaFluor 555 conjugated anti-mouse IgG at 4° C. followed by AlexaFluor 488 conjugated anti-mouse IgG with or without cell permeabilization by saponin (SAP) treatment. Merged images of the AlexaFluor-labeled images are shown in FIG. 20. ScFvA exhibited both surface and intracellular labeling (compare scFvA labeling with (top left) and without (top middle) saponin treatment). In contrast, ScFvD (top right) exhibited only surface labeling upon saponin treatment. There was no labeling with 4-4-20 control scFv (bottom right). These results indicate that scFvA was rapidly internalized into vesicular structures within the RBE4 cells, whereas scFvD and scFvF bound the RBE4 surface but did not promote internalization. As a point of reference the OX26 MAb (FIG. 20, bottom left) has been demonstrated to endocytose and transcytose across brain endothelial cells in vitro and in vivo. As noted, FIG. 17 displays analogous data further illustrating micrographs of dual fluorescent staining of RBE4 binding scFv's showing specific binding and internalization of scFv A by RBE4 cells but not scFv D.

The inventors determined that class 1 scFv exhibited a clear binding signal with either supernatant or purified material at 3-4 µg/mL, but class 2 (scFvD) and 3 scFv (scFvF) required approximately 10-fold higher purified concentrations of 20-80 µg/mL to yield cell surface immunolabeling. In terms of binding affinity to live RBE4 cells, class 1 scFvA possessed an affinity of Kd=82±15 nM, whereas the affinity of class 2 scFvD as a monomeric protein could not be determined using this method. Instead, the inventors evaluated the binding properties of scFvD after predimerization with an epitope tag antibody (avidity=2.0±0.1 nM). As a comparison, the affinity of an anti-transferrin receptor scFv isolated using phagemid panning was measured to be 135 nM, of similar affinity to scFvA isolated with our yeast panning system.

Figure 18:
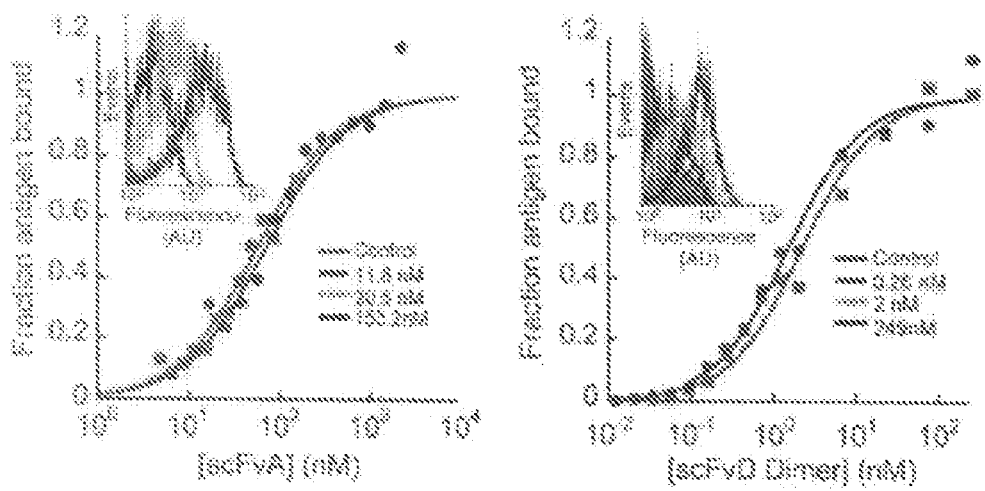
FIG. 18 provides equilibrium binding attributes of scFvA and scFvD. Left panel: binding isotherm for scFvA interaction with live RBE4 cells. The plot shows the fitted monomeric equilibrium binding functions and experimental data from two independent experiments. Right panel: binding isotherm for dimerized scFvD interaction with RBE4 cells. The plot shows the fitted monomeric equilibrium binding functions used to generate an apparent affinity (avidity) and experimental data from two independent experiments. Insets indicate raw flow cytometry histograms that were used to generate the binding curves.

FIG. 18 provides equilibrium binding attributes of scFvA and scFvD. The left panel of FIG. 18 depicts the binding isotherm for scFvA interaction with live RBE4 cells. The plot shows the fitted monomeric equilibrium binding functions and experimental data from two independent experiments. The right panel of FIG. 18 provides the binding isotherm for dimerized scFvD interaction with RBE4 cells. The plot shows the fitted monomeric equilibrium binding functions used to generate an apparent affinity (avidity) and experimental data from two independent experiments. Insets illustrate raw flow cytometry histograms that were used to generate the binding curves.

Thus, the results disclosed herein clearly indicate that yeast culture supernatants can be used directly for facile biochemical testing similar to approaches that use hybridoma-conditioned medium as a source for MAb. Further, the scFv can be purified for labeling and transport studies using the c-terminal six histidine epitope as described in EXAMPLE 11.

Example 10

Immunoprecipitation of Antigens for scFv

Figure 19:
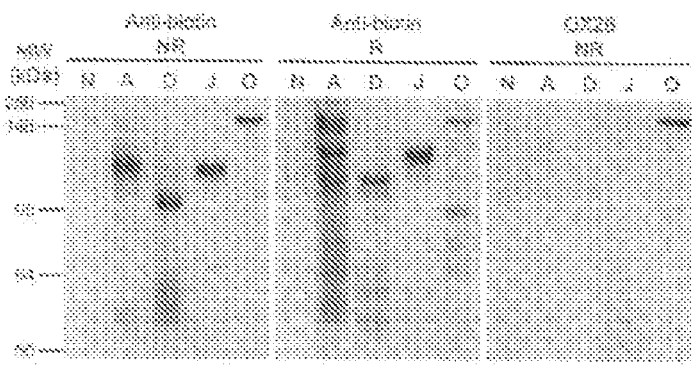
FIG. 19 depicts yeast display immunoprecipitation of antigens for scFvA (A), scFvD (D), scFvJ (J) and OX26 scFv (O). Irrelevant anti-hen egg lysozyme scFv (N) was used as a negative control. The immunoprecipitation products were resolved by either nonreducing (NR) or reducing (R) gel electrophoresis and were probed with an anti-biotin antibody or an anti-transferrin receptor antibody (OX26).

To assess the nature of the antigens recognized by the scFv, the inventors developed a novel yeast immunoprecipitation procedure. They used yeast displaying scFv to directly immunoprecipitate the cognate plasma membrane antigens from detergent-solubilized, biotinylated RBE4 lysates. Conveniently, the use of yeast as the immunoprecipitation particle allowed the sizing of antigens without any additional subcloning, production or immobilization of scFv proteins required by traditional immunoprecipitation methods. The inventors assessed the immunoprecipitated products by anti-biotin Western blotting (FIG. 19), and the low amount of background in such blots was a direct indicator of the specificity of the immunoprecipitation process. The antigens immunoprecipitated by class 1 scFvA (124 kDa-nonreduced, several large molecular weight bands-reduced), class 2 scFvD (104 kDa-nonreduced, 117 kDa-reduced) and class 6 scFvJ (122 kDa-nonreduced, 127 kDa-reduced) were distinct (FIG. 19). As predicted by the homology-based scFv class assignment, other class 1 scFv (scFvB, scFvC, scFvG and scFvK) yielded immunoprecipitation products identical to that seen for scFvA, and class 2 scFv I like that observed for class 2 scFvD (data not shown). The multiple bands appearing in the reduced scFvA sample suggest that along with the antigen recognized specifically by scFvA, co-immunoprecipitation of other biotinylated members of a protein complex or possibly multiple specific antigens may be occurring. Accordingly, scFv-antigen systems were identified that represent novel antibody-blood brain barrier transporter combinations that will form the basis for drug delivery.

Example 11

Purified scFvA Labels the Brain Vasculature in Vivo

Figure 21:
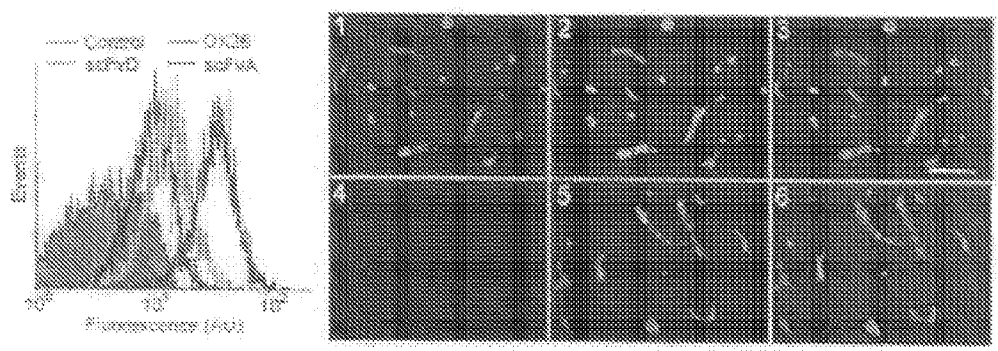
FIG. 21 are fluorescence micrographs showing that scFv A recognizes a brain endothelial antigen expressed in vivo. Frozen rat brain sections were co-labeled with scFvA (1) or 4-4-20 (4) and the brain endothelial cell marker GSA-FITC (2, 5). (3, 6) are merged images indicating the overlap between scFv and GSA-FITC labeling. In contrast to scFvA, irrelevant scFv 4-4-20 did not yield any labeling. Similar results were observed for mouse brain sections and freshly isolated capillaries. Finally, much like the ranking of antigen density for RBE4 cultures, qualitative labeling intensities indicated that the scFvA antigen density in vivo was higher than that for the transferrin receptor (data not shown). Scale bar: 50 μm.

The high-throughput method described so far allowed the identification of scFv clones that bind specifically to RBE4 cells and may be endocytosed in culture. However, the inventors wanted to confirm that clones identified in culture also bound brain endothelial cells in vivo. Therefore, it was necessary to first confirm that the antigen targeted by scFvA in culture was also present on the endothelial cells in vivo. FIG. 21 depicts the assessment of scFvA target antigen density and brain localization. Specifically, the left panel illustrates flow cytometric assessment of antigen density on RBE4 cells. Anti-transferrin receptor monoclonal antibody (OX26), IgG2a isotype control (not shown), pre-dimerized scFvA, pre-dimerized scFvD, and pre-dimerized control 4-4-20 scFv were used at antigen-saturating concentrations to label RBE4 cells in order to make direct comparisons of antigen density. The relative number of antigen sites present on the RBE4 cells was then assessed by flow cytometry. The scFvA antigen was present at approximately 3-fold higher levels than that found for scFvD, and 5.5-fold greater than that observed for the transferrin receptor. Also, the OX26 monoclonal antibody did not compete with scFvA in immunolabeling experiments, nor was the transporter-scFvA interaction sensitive to glycosylation status as deglycosylation of RBE4 cells (mannosidase and neuraminidase) prior to binding had no observable effect.

The right panel of FIG. 21 demonstrates that ScFvA preferentially recognizes the brain microvasculature. Co-localization of scFvA labeling with the highly brain capillary-specific lectin, *Griffonia simplicifolia* agglutinin (GSA) was complete and indicated that all brain blood vessels express the scFvA antigen. Frozen rat brain sections were co-labeled with scFvA (image 1) or 4-4-20 (image 4) and the brain endothelial cell marker GSA-FITC (images 2, 5). Images 3 and 6 are merged images indicating the overlap between scFv and GSA-FITC labeling. In contrast to scFvA, irrelevant scFv 4-4-20 did not yield any labeling. Similar results were observed for mouse brain sections and freshly isolated capillaries. Finally, much like the ranking of antigen density for RBE4 cultures, qualitative labeling intensities indicated that the scFvA antigen density in vivo was higher than that for the transferrin receptor (data not shown). The scale bar provided in image 3 is 50 μm in length. Therefore, scFvA specifically labels the vascular component of brain tissue in vivo and the antigen is of endothelial origin.

Example 12

Materials and Methods

The following provides a detailed description of the materials and methods utilized in the foregoing example sections.

Growth and Induction of scFv Library.

The nonimmune human scFv library in EBY100 yeast8 (a, GAL1-AGA1::URA3 ura3-52 trp1 leu2Δ1 his3Δ200 pep4::HIS2 prb1Δ1.6R can1 GAL) was grown at 30° C. in SD-CAA (20.0 g/L dextrose, 6.7 g/L yeast nitrogen base, 5.0 g/L casamino acids, 10.19 g/L $Na_2HPO_4.7H_2O$, 8.56 g/L $NaH_2PO_4.H_2O$) plus 50 μg/mL kanamycin for 24 hours (OD600~10). Yeast at 10-fold excess of the library diversity ($5\times10^9$) were subsequently induced in 500 mL SG-CAA medium (same as SD-CAA except dextrose replaced by galactose) at 20° C. for 22 hours prior to panning against RBE4 monolayers.

Panning of scFv Library against RBE4 Cell Monolayers.

The RBE4 rat brain endothelial cell line was used as the brain endothelial cell source as RBE4 cells have previously been demonstrated to display many attributes characteristic of the BBB in vivo. RBE4 cells exhibit a nontransformed phenotype, express typical endothelial markers, respond to astrocyte cues, and exhibit BBB-specific properties such as the expression and correct localization of the tight junction protein occludin. In addition, plasma membrane-localized transporters characteristic to brain endothelial cells including those that transport glucose (GLUT1), large neutral amino acids (LAT1), and iron (transferrin receptor), and those that function in active efflux at the BBB (p-glycoprotein, MDR1), are expressed by RBE4 cells. RBE4 cells were a kind gift from Dr. Françoise Roux and were maintained as described previously. RBE4 cells were seeded on collagen type I-coated (Sigma) 6-well plates at 25% confluency two days prior to panning. Induced yeast cells at 10-fold excess of the library size ($5\times10^9$ yeast) were washed twice with 0.01 M PBS, pH 7.4, supplemented with 1 mM $CaCl_2$, 0.5 mM $Mg_2SO_4$ and 0.1% bovine serum albumin (BSA) (Wash buffer) and the yeast mixture was added dropwise onto 100 $cm^2$ of RBE4 cell monolayer to ensure even distribution across the monolayer. The density of yeast ($5\times10^7$ yeast/$cm^2$) is at the upper limit for panning in that the yeast completely coat the RBE4 monolayer. Panning at high density allows ~30% recovery of binding yeast while also providing appropriate oversampling of the library diversity. The monolayers were then incubated at 4° C. for 2 hours to allow yeast-RBE4 cell contacting. The washing strategy was optimized to recover a model scFv that binds to RBE4 cells with nanomolar affinity. The resulting method involved washing the RBE4 layers with ice cold wash buffer by gently rocking the plate twenty-five times, rotating the plate five times (repeated twice), and rotating the plate ten times. The washing supernatant was removed after each step and replaced with fresh wash buffer. After the washing steps, 1 mL of wash buffer was added into each well and all cells were scraped off the plate and pooled together. The yeast/RBE4 cell mixture was resuspended in 5 mL kanamycin-supplemented SD-CAA and grown at 30° C. overnight, followed by SG-CAA induction for 20 hours at 20° C. In parallel, a small fraction of the recovered cells were plated on SD-CAA agar plate to quantify the total number of recovered yeast cells after each round. Since the pool diversity was greatly reduced after round 1, the yeast panning density was lowered to $5\times10^6$ yeast/$cm^2$, and the RBE4 area was reduced to 20 $cm^2$ for round 2 and 10 $cm^2$ for rounds 3-5. After round 2 of panning, the recovered yeast clones numbered $8.2\times10^4$, and a parallel experiment with control yeast displaying an anti-fluorescein scFv (4-4-20) showed very little background using the same washing regimen indicating that the panning strategy was yielding primarily RBE4-binding yeast clones. To confirm that the yeast-RBE4 interactions were scFv-based, the scFv-encoding plasmids for several RBE4-binding yeast clones (7 from round 3, 12 from round 4) were recovered using the Zymoprep yeast miniprep kit (Zymo Research). The scFv-encoding plasmid was then retransformed into yeast surface display parent strain, EBY100, using the lithium acetate method and Trp+ transformants were selected. After RBE4 binding with the retransformed clones was confirmed, the plasmids were sequenced with the Gal1-10 (5'-CAACAAAAAATTGTTAATATACCT-3'; SEQ ID NO:35) and alpha terminator primers (5'-GTTACATCTA-CACTGTTGTTAT-3'; SEQ ID NO: 36) (UW-Madison Biotechnology Center).

High-throughput Analysis of Recovered Yeast Clones.

As described above, yeast are typically grown first in SD-CAA followed by SG-CAA to promote scFv expression. However, this technique yielded comparatively low levels of scFv surface expression level and lowered percentages of yeast displaying scFv when a 96-well format was used. Therefore, the scFv display methodology was optimized for 96-well plates, and it was found that simultaneous growth and induction in SG-CAA allowed for scFv display having similar efficiency to that observed using the traditional yeast display methods. Thus, for high throughput screening, yeast clones were inoculated into 200 μL of SG-CAA (induced sample) and SD-CAA (control uninduced sample) in a 96-well plate and incubated at 30° C. for 24 hours. After removing 160 μL of SD culture to ensure similar total yeast numbers as the parallel SG culture, the 96-well plate of yeast was centrifuged, and the supernatant was carefully removed. The yeast were then washed once with 150 μL wash buffer and resuspended in 150 μL wash buffer. In parallel, RBE4 cells cultured to confluency in a 96-well plate were washed once with ice-cold wash buffer. The yeast clones were then transferred into corresponding wells containing RBE4 monolayers and incubated at 4° C. for 2 hours. After washing, light microscopy was used to assess the binding capacity of the scFv yeast clones. After visual inspection, a yeast clone was defined as RBE4-binding if induced yeast remained bound while uninduced yeast originating from the same clone were washed away.

The scFv genes harbored by binding yeast clones were directly amplified by whole yeast cell PCR. Briefly, a small amount of a fresh, uninduced yeast colony was transferred into 30 μL 0.2% SDS, vortexed, frozen at −80° C. for 2 minutes and incubated at 95° C. for 2 minutes (temperature shift repeated once). One microliter of the cell lysis solution was then used as a PCR reaction template with primers, PNL6 Forward (5'-GTACGAGCTAAAAGTACAGTG-3'; SEQ ID NO: 37) and PNL6 Reverse (5'-TAGATACCCATAC-GACGTTC-3'; SEQ ID NO: 38). Subsequently, 20 μL of PCR product was subjected to BstNI (New England Biolabs) restriction digest at 60° C. for 14 hours. The digested products were resolved on a 3% agarose gel for unique scFv clone identification. The PCR product of each clone displaying a unique BstNI digestion pattern was sequenced with Rev Seq P2 (5'-CCGCCGAGCTATTACAAGTC-3'; SEQ ID NO: 39) and For Seq P2 (5'-TCTGCAGGCTAGTGGTGGTG-3'; SEQ ID NO: 40) primers. The sequence was then analyzed by the IgBLAST program to identify the human germline origin (IgBLAST available at NCBI website: www.ncbi.nlm.nih.gov).

Yeast Colony Northern Blotting.

Yeast colony Northern blotting was used to detect and presubtract class 1 and class 2 scFv from the yeast binding pool. Reagents and instruments were prepared as in standard Northern blotting experiments to eliminate RNase contamination. Yeast clones were cultured on SD-CAA agar plates and the resulting colonies were transferred onto ethanol-sterilized nitrocellulose membranes. The colony-loaded membrane was then layered on top of SG-CAA agar plates, cell side facing up, and incubated at 30° C. for 2 days to induce transcription of the scFv gene. To prepare the induced yeast colonies for Northern blotting, the nitrocellulose membranes were layered onto Whatman filter paper soaked with 10% SDS and incubated at 65° C. for 30 minutes. The filters were then fixed by transferring to formaldehyde-soaked filter paper at 65° C. for 30 minutes (3×SSC, 10% formaldehyde in ddH$_2$O). Air-dried membranes were subsequently baked for 2 hours at 80° C. under vacuum. Oligonucleotide probes corresponding to Class 1 VHCDR2 and Class 2 VHCDR2 were radiolabeled with a 10 residue $32^P$-dATP tail using the STAR-FIRE kit according to manufacturer's instructions (IDT), and their specific radioactivity was determined by scintillation counting. Being part of the germline V-region, the VHCDR2 regions exhibited 100% homology within class 1 and class 2, and were therefore amenable to hybridization-based subtraction. The membranes were blocked in prehybridization buffer (50% formamide, 5× Denhardt's solution, 5×SSPE, 1% SDS, 0.1% salmon sperm DNA) at 43° C. for 2 hours, and then hybridized (prehybridization buffer with 8×105 cpm/ml of each probe) at 43° C. overnight. After hybridization, the nitrocellulose membranes were washed as follows: 2×SSC, 0.1% SDS at room temperature for 8 minutes, 0.5×SSC, 0.1% SDS at room temperature for 8 minutes, 0.1×SSC, 0.1% SDS at room temperature for 8 minutes, 0.1×SSC, 1% SDS at 50° C. for 30 minutes. The membranes were then exposed to ECL Hyperfilm (Amersham) at −80° C. for 24 or 72 hours. Although VHCDR2 was used as the probe in these subtractive screens, the diversity of the recovered scFv clones can be readily expanded as desired via subtraction using any combination of CDR probes.

ScFv Secretion and Purification.

Open reading frames for scFv were isolated from the PCR products used for BstNI typing by NheI-HindIII restriction digest and were shuttled to an scFv yeast secretion vector (pRS316-GAL4-4-20) that has been used extensively for scFv secretion. The resultant pRS316-GALscFv plasmids were then transformed into YVH10, a yeast strain overexpressing protein disulfide isomerase. Yeast harboring scFv secretion vector were grown in minimal SD medium (2% dextrose, 0.67% yeast nitrogen base) supplemented with 2×SCAA amino acid (190 mg/L Arg, 108 mg/L Met, 52 mg/L Tyr, 290 mg/L Ile, 440 mg/L Lys, 200 mg/L Phe, 1260 mg/L Glu, 400 mg/L Asp, 480 mg/L Val, 220 mg/L Thr, 130 mg/L Gly, 20 mg/L tryptophan lacking leucine and uracil) at 30° C. for 72 hours. Subsequently, scFv secretion was induced at 20° C. for 72 hours in SG-SCAA (dextrose substituted by galactose) with 1 mg/ml BSA as a nonspecific carrier. For experiments requiring purified scFv, Ni-NTA columns (Qiagen) were used to purify the six histidine-tagged scFv from 50 mL or 1 L batches as described previously in the literature.

The size, purity, and secretion yields of scFv were analyzed by SDS-polyacrylamide gel electrophoresis (PAGE) with a 4% stacking and 12.5% separating gel followed by Coomassie blue staining. Protein concentrations were estimated by comparison to a series of carbonic anhydrase standards (31 kDa) and by BCA protein assay (Pierce). In parallel, the SDS-PAGE resolved proteins were also blotted onto a nitrocellulose membrane (BioRad) for Western blotting. The nitrocellulose membrane was blocked at 4° C. overnight in TBST solution (8 g/L NaCl, and 0.1% Tween-20, buffered to pH 7.6 with 20 mM Tris) supplemented with 5% nonfat milk and probed with 1 μg/mL 9E10 anti c-myc antibody (Covance) followed by an anti-mouse IgG horse radish peroxidase conjugate (Sigma). Detection was performed using enhanced chemiluminescence and multiple time point exposures to ECL hyperfilm (Amersham) were evaluated by NIH ImageJ software for quantification.

Affinity Determination.

RBE4 cells were labeled at various scFvA concentrations at 4° C., and the bound scFv detected by anti-cmyc (9E10) antibody labeling followed by anti-mouse IgG AlexaFluor 555. Fluorescence intensity was monitored by FACSCalibur flow cytometer and used to quantitate fractional bound ligand. The scFvA binding data was fit to an equilibrium binding model to determine the monovalent affinity dissociation constant (Kd). The cell-labeling assay was not sensitive enough to produce a binding curve using monomeric scFvD, so scFvD was predimerized with anti-epitope tag antibody, 9E10, to provide the requisite avidity for the ligand binding measurements. ScFv D dimer-labeled cells were then probed with anti-mouse IgG AlexaFluor 555 conjugate and assessed by flow cytometry. The resulting data was fit to an equilibrium binding model to derive an apparent affinity (avidity). For antigen density experiments, living RBE4 cells were labeled at 4° C. with 62.5 nM of pre-dimerized scFvA, scFvD, 4-4-20 scFv, OX26 monoclonal antibody, or IgG2a isotype control. A uniform secondary antibody (anti-mouse IgG AlexaFluor 555 conjugate) was used for each sample to facilitate quantitative comparisons of labeling intensity. These antibody labeling concentrations were adequate for saturation binding of the cell surface antigens, and the cell surface labeling was quantitatively assessed by flow cytometry.

ScFv-RBE4 Immunocytochemistry.

Predimerization of scFv via the c-myc epitope tag by the 9E 10 antibody was used as a method to provide bivalency which is often an important component for promoting cellular internalization of scFv. To this end, the RBE4-binding scFv was first incubated with 9E10 to form artificial dimers. Equal volumes of purified scFv (diluted to 8 µg/mL for scFvA or 32 µg/mL for scFvD and 4-4-20 using 40% goat serum in PBS supplemented with 1 mM $CaCl_2$, 0.5 mM $Mg_2SO_4$) and 10 µg/mL 9E10 were mixed and incubated at room temperature for 1 hour to form artificial dimer. RBE4 cells at about 90% confluency were washed 3× with wash buffer. RBE4 cells were then incubated with scFv artificial dimer or OX26 monoclonal antibody (10 µg/mL) (Serotec) at 4° C. for 30 minutes and then switched to 37° for another 30 minutes. An anti-mouse IgG secondary antibody conjugated with Alexa-Flour555 (Molecular Probes) was applied for 30 minutes at 4° C. to label cell surface-bound scFv. The cells were then permeabilized with 0.5% saponin (SigmaAldrich) diluted in wash buffer at 4° C. for 5 minutes, and subsequently labeled with an anti-mouse IgG antibody conjugated with AlexaFluor488 (Molecular Probes) for 30 minutes at 4° C. to detect internalized scFv. Labeled cells were then fixed with 4% paraformaldehyde and examined using a fluorescence microscope (Olympus IX70).

Yeast Display Immunoprecipitation.

ScFv-displaying yeast cells selected from the human scFv library were directly used to immunoprecipitate the cognate plasma membrane antigens. Yeast cells displaying anti-hen egg lysozyme (D1.3) scFv were used as a negative control. As a positive control, an anti-transferrin receptor OX26 scFv yeast display plasmid was created by excising OX26 scFv open reading frame from pRS316-GALOX26 as an NheI-XhoI fragment and ligating into pCT-LWHI. Yeast clones were grown and induced in 50 ml cultures as described above. Induced yeast were collected by centrifugation, washed and fixed with 3% vol/vol formalin in PBS. RBE4 plasma membrane proteins were biotinylated using 0.5 mg/mL Sulfo-NHS-LC-Biotin (Pierce). To prepare RBE4 cell lysate, approximately $5×10^6$ biotinylated RBE4 cells were lysed using a 1% (w/v) n-octyl-beta-D-glucopyranoside (scFvA, B, C and J Sigma) or 0.1% (w/v) Triton X-100 (scFvD, I, J, and OX26, Sigma) detergent solution in PBS, supplemented with a protease inhibitor cocktail (Calbiochem). For immunoprecipitation, 400 µg of cell lysate protein was mixed with approximately $10^8$ yeast cells and incubated overnight at 4° C. Elution of immunoprecipitated product was performed by resuspending yeast cells in 30 µL of 0.5% SDS in 0.4 M Tris (pH 6.8) for 15 minutes. The eluates were separated with SDS-PAGE (8% separating gel) with or without reducing agent (DTT) present, and blotted onto a nitrocellulose membrane (BioRad). Western blotting was subsequently performed with an anti-biotin monoclonal antibody (0.5 µg/mL, clone BTN.4, Labvision), OX26 monoclonal antibody (5 µg/mL, Serotec), or anti-insulin receptor □-subunit monoclonal antibody (1 µg/mL, clone CT-3, Labvision) as described above. Neither scFvA nor scFvD were active in Western blotting format with immunoprecipitated products or with cell lysates, likely a result of selections being performed under native conditions with living cells.

Immunohistochemical Labeling of Rat Brain Sections by scFv A.

Brain tissue sections were prepared from the brain of an adult male Sprague Dawley rat. The brain was snap-frozen with tissue freezing medium (Triangle Biomedical Sciences) using a liquid nitrogen bath, and 7 µm coronal sections were cut from the frozen brain. The brain sections were blocked with 40% goat serum and 0.2% TritonX-100 in PBSCM at room temperature for 30 minutes. Purified scFv A or 4-4-20 was diluted with 40% goat serum and incubated with an equal volume of 10 µg/mL 9E10 for 1 hour at room temperature to form artificial dimer. Brain sections were then incubated with scFv A artificial dimer at 4° C. for 1 hour. A secondary labeling solution consisting of phycoerythrin-conjugated anti-mouse IgG and FITC conjugated *Griffonia simplicifolia* lectin (GSA-FITC 10 µg/ml, Sigma) was applied for 30 minutes at 4° C. After washing, the brain sections were immediately fixed with 4% paraformaldehyde for 10 minutes on ice and examined by fluorescence microscopy.

As described in the preceding EXAMPLES, the invention provides a method of panning a yeast display antibody library against cultured endothelial cells and simultaneously isolating multiple binders of different affinities against one or more antigens. The binding clones were isolated and their ability to trigger endocytosis and transcytosis was then confirmed using endothelial cells.

While this invention has been described in conjunction with the various exemplary embodiments outlined above, various alternatives, modifications, variations, improvements, and/or substantial equivalents, whether known or that are or may be presently unforeseen, may become apparent to those having at least ordinary skill in the art. Accordingly, the exemplary embodiments according to this invention, as set forth above, are intended to be illustrative, not limiting. Various changes may be made without departing from the spirit and scope of the invention. Therefore, the invention is intended to embrace all known or later-developed alternatives, modifications, variations, improvements, and/or substantial equivalents of these exemplary embodiments.

What is claimed is:

1. An isolated polypeptide comprising an antibody fragment having an amino acid sequence set forth in any one of SEQ ID NOs. 1-5.

2. The isolated polypeptide of claim 1, wherein the antibody fragment has the amino acid sequence set forth in SEQ ID NO. 1.

3. The isolated polypeptide of claim 1, wherein the antibody fragment binds to a brain endothelial cell.

4. The isolated polypeptide of claim 1, wherein the antibody fragment is a single chain fragment variable (scFv) antibody.

5. A composition comprising: an isolated antibody fragment set forth in any one of SEQ ID NOs. 1-5 and a pharmaceutically active compound linked thereto.

6. The composition of claim 5, wherein the antibody fragment is set forth in SEQ ID NO. 1.

* * * * *

UNITED STATES PATENT AND TRADEMARK OFFICE
CERTIFICATE OF CORRECTION

PATENT NO. : 7,744,879 B2  Page 1 of 1
APPLICATION NO. : 11/759723
DATED : June 29, 2010
INVENTOR(S) : Eric V. Shusta, X. Wang and Yongku P. Cho It is certified that error appears in the above-identified patent and that said Letters Patent is hereby corrected as shown below:

Col. 1, lines 12-17 should read

STATEMENT REGARDING FEDERALLY SPONSORED RESEARCH AND DEVELOPMENT
This invention was made with government support under NS052649 awarded by the National Institutes of Health and 0238864 awarded by the National Science Foundation. The government has certain rights in the invention.

Signed and Sealed this

Seventeenth Day of August, 2010

David J. Kappos
*Director of the United States Patent and Trademark Office*

SEQUENCE LISTING

<160> NUMBER OF SEQ ID NOS: 40

<210> SEQ ID NO 1
<211> LENGTH: 264
<212> TYPE: PRT
<213> ORGANISM: Homo sapiens

```
<400> SEQUENCE: 1

Ala Ser Glu Val Gln Leu Leu Glu Ser Gly Gly Asp Leu Ile Gln Ser
1               5                   10                  15

Gly Gly Ser Leu Arg Leu Ser Cys Ala Ala Ser Gly Phe Thr Val Thr
            20                  25                  30

Ser Asn Tyr Met Asn Trp Val Arg Gln Ala Pro Gly Lys Gly Leu Glu
        35                  40                  45

Trp Val Ser Leu Ile Tyr Ser Gly Gly Ser Thr Ser Tyr Ala Asp Ser
    50                  55                  60

Val Lys Gly Arg Phe Thr Ile Ser Arg Asp Asn Ser Asn Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Gly Arg Pro Asn Trp Tyr Phe Asp Leu Trp Gly Arg Gly
            100                 105                 110

Thr Leu Val Thr Val Ser Ser Gly Ile Leu Gly Ser Gly Gly Gly Gly
            115                 120                 125

Ser Gly Gly Gly Ser Gly Gly Gly Ser Gln Ser Val Leu Thr
            130                 135                 140

Gln Pro Ala Ser Val Ser Gly Ser Pro Gly Gln Ser Ile Thr Ile Ser
145                 150                 155                 160

Cys Thr Gly Thr Ser Arg Asp Ile Gly Ala Tyr Asn Tyr Val Ser Trp
            165                 170                 175

Tyr Gln Gln His Pro Gly Lys Ala Pro Lys Val Met Ile Tyr Asp Val
            180                 185                 190

Ser Lys Arg Pro Ser Gly Val Pro Asp Arg Phe Ser Gly Ser Lys Ser
            195                 200                 205

Gly Asn Thr Ala Ser Leu Thr Ile Ser Gly Leu Gln Ala Glu Asp Glu
            210                 215                 220

Ala Asp Tyr Tyr Cys Ser Ser Tyr Thr Ser Ser Ser Thr Pro His Val
225                 230                 235                 240

Val Phe Gly Gly Gly Thr Lys Leu Thr Val Leu Ser Gly Ile Leu Glu
                245                 250                 255

Gln Lys Leu Ile Ser Glu Glu Asp
            260

<210> SEQ ID NO 2
<211> LENGTH: 263
<212> TYPE: PRT
<213> ORGANISM: Homo sapiens

<400> SEQUENCE: 2

Ala Ser Glu Val Gln Leu Leu Glu Ser Gly Gly Asp Leu Ile Gln Ser
1               5                   10                  15

Gly Gly Ser Leu Arg Leu Ser Cys Ala Ala Ser Gly Phe Thr Val Thr
            20                  25                  30

Ser Asn Tyr Met Asn Trp Val Arg Gln Ala Pro Gly Lys Gly Leu Glu
        35                  40                  45

Trp Val Ser Leu Ile Tyr Ser Gly Gly Ser Thr Ser Tyr Ala Asp Ser
    50                  55                  60

Val Lys Gly Arg Phe Thr Ile Ser Arg Asp Asn Ser Asn Asn Thr Leu
65                  70                  75                  80

Tyr Leu Gln Met Asn Ser Leu Arg Ala Glu Asp Thr Ala Val Tyr Tyr
                85                  90                  95
```

```
Cys Ala Arg Gly Arg Pro Asn Trp Tyr Phe Asp Leu Trp Gly Arg Gly
            100                 105                 110

Thr Leu Val Thr Val Ser Ser Gly Ile Leu Gly Ser Gly Gly Gly Gly
            115                 120                 125

Ser Gly Gly Gly Gly Ser Gly Gly Gly Ser Gln Ser Val Leu Thr
130                 135                 140

Gln Pro Ala Ser Val Ser Gly Ser Pro Gly Gln Ser Ile Thr Ile Ser
145                 150                 155                 160

Cys Thr Gly Thr Ser Arg Asp Ile Gly Ala Tyr Asn Tyr Val Ser Trp
                165                 170                 175

Tyr Gln Gln His Pro Gly Lys Ala Pro Lys Val Met Ile Tyr Asp Val
                180                 185                 190

Ser Lys Arg Pro Ser Gly Val Pro Asp Arg Phe Ser Gly Ser Lys Ser
                195                 200                 205

Gly Asn Thr Ala Ser Leu Thr Ile Ser Gly Leu Gln Ala Glu Asp Glu
            210                 215                 220

Ala Asp Tyr Tyr Cys Ser Ser Tyr Thr Asn Ser Ser Thr Pro His Val
225                 230                 235                 240

Val Phe Gly Gly Gly Thr Gln Leu Thr Val Leu Ser Ile Leu Glu
                245                 250                 255

Gln Lys Leu Ile Ser Glu Glu
            260

<210> SEQ ID NO 3
<211> LENGTH: 263
<212> TYPE: PRT
<213> ORGANISM: Homo sapiens

<400> SEQUENCE: 3

Ala Ser Glu Val Gln Leu Leu Glu Ser Gly Gly Asp Leu Ile Gln Ser
1               5                   10                  15

Gly Gly Ser Leu Arg Leu Ser Cys Ala Ala Ser Gly Phe Thr Val Thr
            20                  25                  30

Ser Asn Tyr Met Asn Trp Val Arg Gln Ala Pro Gly Lys Gly Leu Glu
            35                  40                  45

Trp Val Ser Leu Ile Tyr Ser Gly Ser Thr Ser Tyr Ala Asp Ser
        50                  55                  60

Val Lys Gly Arg Phe Thr Ile Ser Arg Asp Asn Ser Asn Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Gly Arg Pro Asn Trp Tyr Phe Asp Leu Trp Gly Arg Gly
            100                 105                 110

Thr Leu Val Thr Val Ser Ser Gly Ile Leu Gly Ser Gly Gly Gly Gly
            115                 120                 125

Ser Gly Gly Gly Gly Ser Gly Gly Gly Ser Gln Ser Val Leu Thr
130                 135                 140

Gln Pro Ala Ser Val Ser Gly Ser Pro Gly Gln Ser Ile Thr Ile Ser
145                 150                 155                 160

Cys Thr Gly Thr Ser Arg Asp Ile Gly Ala Tyr Asn Tyr Val Ser Trp
                165                 170                 175

Tyr Gln Gln His Pro Gly Lys Ala Pro Lys Val Met Ile Tyr Asp Val
                180                 185                 190

Ser Lys Arg Pro Ser Gly Val Pro Asp Arg Phe Ser Gly Ser Lys Ser
                195                 200                 205
```

```
Gly Asn Thr Ala Ser Leu Thr Ile Ser Gly Leu Gln Ala Glu Asp Glu
        210                 215                 220

Ala Asp Tyr Tyr Cys Ser Ser Tyr Thr Ser Ser Ser Thr Pro His Val
225                 230                 235                 240

Val Phe Gly Gly Gly Thr Asn Val Thr Val Leu Ser Gly Ile Leu Glu
                245                 250                 255

Gln Lys Leu Ile Ser Glu Glu
            260
```

<210> SEQ ID NO 4
<211> LENGTH: 265
<212> TYPE: PRT
<213> ORGANISM: Homo sapiens

<400> SEQUENCE: 4

```
Ala Ser Glu Val Gln Leu Leu Glu Ser Gly Gly Asp Leu Ile Gln Ser
1               5                   10                  15

Gly Gly Ser Leu Arg Leu Ser Cys Ala Ala Ser Gly Phe Thr Val Thr
            20                  25                  30

Ser Asn Tyr Met Asn Trp Val Arg Gln Ala Pro Gly Lys Gly Leu Glu
        35                  40                  45

Trp Val Ser Leu Ile Tyr Ser Gly Gly Ser Thr Ser Tyr Ala Asp Ser
    50                  55                  60

Val Lys Gly Arg Phe Thr Ile Ser Arg Asp Asn Ser Asn Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Gly Arg Pro Asn Trp Tyr Phe Asp Leu Trp Gly Arg Gly
            100                 105                 110

Thr Leu Val Thr Val Ser Ser Gly Ile Leu Gly Ser Gly Gly Gly Gly
        115                 120                 125

Ser Gly Gly Gly Gly Ser Gly Gly Gly Ser Gln Ser Val Leu Thr
    130                 135                 140

Gln Pro Ala Ser Val Ser Gly Ser Pro Gly Gln Ser Ile Thr Ile Ser
145                 150                 155                 160

Cys Thr Gly Thr Ser Arg Asp Ile Gly Ala Tyr Asn Tyr Val Ser Trp
                165                 170                 175

Tyr Gln Gln His Pro Gly Lys Ala Pro Arg Val Met Ile Tyr Asp Val
            180                 185                 190

Ser Lys Arg Pro Ser Gly Val Pro Asp Arg Phe Ser Gly Ser Lys Ser
        195                 200                 205

Gly Asn Thr Ala Ser Leu Thr Ile Ser Gly Leu Gln Ala Glu Asp Glu
        210                 215                 220

Ala Asp Tyr Tyr Cys Ser Ser Tyr Thr Gly Ser Ser Thr Pro His Val
225                 230                 235                 240

Val Phe Gly Gly Gly Thr Pro Leu Thr Val Leu Ser Gly Phe Leu Glu
                245                 250                 255

Gln Lys Leu Ile Ser Glu Glu Asp Leu
            260                 265
```

<210> SEQ ID NO 5
<211> LENGTH: 249
<212> TYPE: PRT
<213> ORGANISM: Homo sapiens

<400> SEQUENCE: 5

Ala Ser Glu Val Gln Leu Leu Glu Ser Gly Gly Asp Leu Ile Gln Ser
1               5                   10                  15

Gly Gly Ser Leu Asn Ser Pro Val Gln Pro Leu Gly Ser Pro Leu Thr
            20                  25                  30

Ser Asn Tyr Met Asn Trp Val Arg Gln Ala Pro Gly Lys Gly Leu Glu
        35                  40                  45

Trp Val Ser Leu Ile Tyr Ser Gly Gly Ser Thr Ser Tyr Ala Asp Ser
    50                  55                  60

Val Lys Gly Arg Phe Thr Ile Ser Arg Asp Asn Ser Asn Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Gly Arg Pro Asn Trp Tyr Phe Asp Leu Trp Gly Arg Gly
            100                 105                 110

Thr Leu Val Thr Val Ser Ser Gly Ile Leu Gly Ser Gly Gly Gly Gly
            115                 120                 125

Ser Gly Gly Gly Gly Ser Gly Gly Gly Ser Gln Ser Val Leu Thr
130                 135                 140

Gln Pro Ala Ser Val Ser Gly Ser Pro Gly Gln Ser Ile Thr Ile Ser
145                 150                 155                 160

Cys Thr Gly Thr Ser Arg Asp Ile Gly Ala Tyr Asn Tyr Val Ser Trp
            165                 170                 175

Tyr Gln Gln His Pro Gly Lys Ala Pro Lys Val Met Ile Tyr Asp Val
            180                 185                 190

Ser Lys Arg Pro Ser Gly Val Pro Asp Arg Phe Ser Gly Ser Lys Ser
            195                 200                 205

Gly Asn Thr Ala Ser Leu Thr Ile Ser Gly Leu Gln Ala Glu Asp Glu
            210                 215                 220

Ala Asp Tyr Tyr Cys Ser Ser Tyr Thr Ser Ser Gln His Ser Pro Cys
225                 230                 235                 240

Gly Phe Gly Gly Gly Pro Leu Thr Val
                245

<210> SEQ ID NO 6
<211> LENGTH: 273
<212> TYPE: PRT
<213> ORGANISM: Homo sapiens

<400> SEQUENCE: 6

Ala Ser Gln Val Gln Leu Gln Gln Ser Gly Pro Gly Leu Val Lys Pro
1               5                   10                  15

Ser Gln Thr Leu Ser Leu Thr Cys Ala Ile Ser Gly Asp Ser Val Ser
            20                  25                  30

Ser Asn Ser Val Ala Trp Asn Trp Ile Arg Gln Ser Pro Ser Arg Gly
        35                  40                  45

Leu Glu Trp Leu Gly Arg Thr Tyr Tyr Arg Ser Lys Trp Tyr Tyr Asp
    50                  55                  60

Tyr Ala Leu Ser Val Lys Ser Arg Ile Thr Ile Asn Pro Asp Thr Ser
65                  70                  75                  80

Lys Asn Gln Phe Ser Leu Gln Leu Asn Ser Val Thr Pro Glu Asp Thr
                85                  90                  95

Ala Ile Tyr Tyr Cys Ala Arg Gln Leu Gly Gly Ser Gly Met Asp Val
            100                 105                 110

Trp Gly Gln Gly Thr Thr Val Thr Val Ser Ser Gly Ser Ala Ser Ala

```
            115                 120                 125
Pro Thr Gly Ile Leu Gly Ser Gly Gly Gly Ser Gly Gly Gly
    130                 135                 140
Ser Gly Gly Gly Ser Ser Tyr Glu Leu Thr Gln Pro Pro Ser Ala
145                 150                 155                 160
Ser Gly Thr Pro Gly Gln Arg Val Thr Ile Ser Cys Ser Gly Ser
                165                 170                 175
Ser Asn Ile Gly Ser Arg Tyr Val Tyr Trp Tyr Gln Gln Leu Pro Gly
            180                 185                 190
Thr Ala Pro Lys Leu Leu Ile Tyr Lys Asn Asn Gln Arg Pro Ser Gly
        195                 200                 205
Val Pro Asp Arg Phe Ser Gly Ser Lys Ser Gly Thr Ser Ala Ser Leu
210                 215                 220
Ala Ile Ser Gly Leu Arg Ser Glu Asp Glu Ala Asp Tyr Tyr Cys Ala
225                 230                 235                 240
Ala Trp Asp Asp Ile Leu Ser Gly Thr Val Phe Gly Gly Gly Thr Gln
                245                 250                 255
Leu Thr Val Leu Ser Gly Ile Leu Glu Gln Lys Leu Ile Ser Glu Glu
            260                 265                 270
Asp

<210> SEQ ID NO 7
<211> LENGTH: 274
<212> TYPE: PRT
<213> ORGANISM: Homo sapiens

<400> SEQUENCE: 7

Ala Ser Gln Val Gln Leu Gln Gln Ser Gly Pro Gly Leu Val Lys Pro
1               5                   10                  15
Ser Gln Thr Leu Ser Leu Thr Cys Asp Ile Ser Gly Asp Ser Val Ser
            20                  25                  30
Ser Asn Ser Ala Ala Trp Asn Trp Ile Arg Gln Ser Pro Ser Arg Gly
        35                  40                  45
Leu Glu Trp Leu Gly Arg Thr Tyr Tyr Arg Ser Lys Trp Tyr Asn Asp
50                  55                  60
Tyr Ala Leu Ser Val Lys Ser Arg Ile Thr Ile Asn Pro Asp Thr Ser
65                  70                  75                  80
Lys Asn Gln Phe Ser Leu His Leu Asn Ser Val Thr Pro Glu Asp Thr
                85                  90                  95
Ala Val Tyr Tyr Cys Ala Arg Gln Leu Gly Gly Ser Gly Met Asp Val
            100                 105                 110
Trp Gly Gln Gly Thr Thr Val Thr Val Ser Ser Gly Ser Ala Ser Ala
        115                 120                 125
Pro Thr Gly Ile Leu Gly Ser Gly Gly Gly Ser Gly Gly Gly Gly
    130                 135                 140
Ser Gly Gly Gly Gly Ser Ser Tyr Glu Leu Thr Gln Pro Pro Ser Ala
145                 150                 155                 160
Ser Gly Thr Pro Gly Gln Arg Val Thr Ile Ser Cys Ser Gly Ser
                165                 170                 175
Ser Asn Ile Gly Ser Arg Tyr Val Tyr Trp Tyr Gln Gln Leu Pro Gly
            180                 185                 190
Thr Ala Pro Lys Leu Leu Ile Tyr Lys Asn Asn Gln Arg Pro Ser Gly
        195                 200                 205
Val Pro Asp Arg Phe Ser Gly Ser Lys Ser Gly Thr Ser Ala Ser Leu
```

```
                210                 215                 220
Ala Ile Ser Gly Leu Arg Ser Glu Asp Glu Ala Asp Tyr Tyr Cys Ala
225                 230                 235                 240

Ala Trp Asp Asp Ile Leu Ser Gly Thr Val Phe Gly Gly Gly Thr Gln
                245                 250                 255

Leu Thr Val Leu Ser Gly Ile Leu Glu Gln Lys Leu Ile Ser Glu Glu
                260                 265                 270

Asp Leu

<210> SEQ ID NO 8
<211> LENGTH: 235
<212> TYPE: PRT
<213> ORGANISM: Homo sapiens

<400> SEQUENCE: 8

Ala Ser Gln Val Gln Leu Gln Gln Ser Gly Pro Gly Leu Val Lys Pro
1               5                   10                  15

Ser Gln Thr Leu Ser Leu Thr Cys Ala Ile Ser Gly Asp Ser Val Ser
                20                  25                  30

Ser Asn Ser Val Ala Trp Asn Trp Ile Arg Gln Ser Pro Ser Arg Gly
            35                  40                  45

Leu Glu Trp Leu Gly Arg Thr Tyr Tyr Arg Ser Lys Trp Tyr Tyr Asp
50                  55                  60

Tyr Ala Leu Ser Val Lys Ser Arg Ile Thr Ile Asn Pro Asp Thr Ser
65                  70                  75                  80

Lys Asn Gln Phe Ser Leu Gln Leu Asn Ser Val Thr Pro Glu Asp Thr
                85                  90                  95

Ala Ile Tyr Tyr Cys Ala Arg Gln Leu Gly Gly Ser Gly Met Asp Val
            100                 105                 110

Trp Gly Gln Gly Thr Thr Val Thr Val Ser Ser Gly Ser Ala Ser Ala
        115                 120                 125

Pro Thr Gly Ile Leu Gly Ser Gly Gly Gly Ser Gly Gly Gly Gly
    130                 135                 140

Ser Gly Gly Gly Gly Ser Ser Tyr Glu Leu Thr Gln Pro Pro Ser Ala
145                 150                 155                 160

Ser Gly Thr Pro Gly Gln Arg Val Thr Ile Ser Cys Ser Gly Gly Ser
                165                 170                 175

Ser Asn Ile Gly Ser Arg Tyr Val Tyr Trp Tyr Gln Gln Leu Pro Gly
            180                 185                 190

Thr Ala Pro Lys Leu Leu Ile Tyr Lys Asn Asn Gln Arg Pro Ser Gly
        195                 200                 205

Val Pro Asp Arg Phe Ser Gly Ser Lys Ser Gly Thr Ser Ala Ser Leu
    210                 215                 220

Ala Ile Ser Gly Leu Arg Ser Glu Asp Gly
225                 230                 235

<210> SEQ ID NO 9
<211> LENGTH: 274
<212> TYPE: PRT
<213> ORGANISM: Homo sapiens

<400> SEQUENCE: 9

Ala Ser Gln Val Gln Leu Gln Gln Ser Gly Pro Gly Leu Val Lys Pro
1               5                   10                  15

Ser Gln Thr Leu Ser Leu Thr Cys Ala Ile Ser Gly Asp Ser Val Ser
                20                  25                  30
```

```
Ser Asn Ser Val Ala Trp Asn Trp Ile Arg Gln Ser Pro Ser Arg Gly
            35                  40                  45

Leu Glu Trp Leu Gly Arg Thr Tyr Tyr Arg Ser Lys Trp Tyr Tyr Asp
 50                  55                  60

Tyr Ala Leu Ser Val Lys Ser Arg Ile Thr Ile Asn Pro Asp Thr Ser
 65                  70                  75                  80

Lys Asn Gln Phe Ser Leu Gln Leu Asn Ser Val Thr Pro Glu Asp Thr
                85                  90                  95

Ala Ile Tyr Tyr Cys Ala Arg Gln Leu Gly Gly Ser Gly Met Asp Val
               100                 105                 110

Trp Gly Gln Gly Thr Thr Val Thr Val Ser Ser Gly Ser Ala Ser Ala
           115                 120                 125

Pro Thr Gly Ile Leu Gly Ser Gly Gly Gly Ser Gly Gly Gly Gly
       130                 135                 140

Ser Gly Gly Gly Gly Ser Ser Tyr Glu Leu Thr Gln Pro Pro Ser Ala
145                 150                 155                 160

Ser Gly Thr Pro Gly Gln Arg Val Thr Ile Ser Cys Ser Gly Gly Ser
               165                 170                 175

Ser Asn Ile Gly Ser Arg Tyr Val Tyr Trp Tyr Gln Gln Leu Pro Gly
           180                 185                 190

Thr Ala Pro Lys Leu Leu Ile Tyr Lys Asn Asn Gln Arg Pro Ser Gly
       195                 200                 205

Val Pro Asp Arg Phe Ser Gly Ser Lys Ser Gly Thr Ser Ala Ser Leu
210                 215                 220

Ala Ile Ser Gly Leu Arg Ser Glu Asp Glu Ala Asp Tyr Tyr Cys Ala
225                 230                 235                 240

Ala Trp Asp Asp Ile Leu Ser Gly Thr Val Phe Gly Gly Gly Thr Ser
               245                 250                 255

Arg Pro Ser Leu Ser Gly Ile Leu Glu Gln Lys Leu Ile Ser Glu Glu
           260                 265                 270

Asp Leu

<210> SEQ ID NO 10
<211> LENGTH: 264
<212> TYPE: PRT
<213> ORGANISM: Homo sapiens

<400> SEQUENCE: 10

Ala Ser Gln Val Pro Leu Val Glu Ser Glu Gly Asp Leu Val Gln Pro
 1               5                  10                  15

Gly Arg Ser Leu Arg Leu Ser Cys Ala Ala Ser Gly Phe Asp Phe Gln
                20                  25                  30

Asn Ser Gly Met His Trp Val Arg Gln Pro Pro Gly Lys Gly Leu Glu
            35                  40                  45

Trp Val Ser Gly Ile Arg Trp Asp Ser Lys Thr Arg Ile Tyr Ala Asp
 50                  55                  60

Ser Val Arg Gly Arg Phe Thr Ile Ser Arg Asp Asn Thr Lys Asn Ser
 65                  70                  75                  80

Leu Tyr Leu Gln Met Asp Asn Leu Arg Pro Glu Asp Thr Ala Leu Tyr
                85                  90                  95

Tyr Cys Val Cys Arg Gly Ser His Phe Gln Phe Asp Phe Trp Gly Gln
               100                 105                 110

Gly Thr Leu Val Thr Val Ser Ser Gly Ile Leu Gly Ser Gly Gly Gly
           115                 120                 125
```

```
Gly Ser Gly Gly Gly Ser Gly Gly Gly Ser Gln Ser Ala Leu
        130                 135                 140

Ile Gln Pro Ala Ser Val Ser Gly Ser Pro Gly Gln Ser Ile Thr Ile
145                 150                 155                 160

Ser Cys Thr Gly Thr Ser Ser Asp Ile Gly Gly Tyr Asn Tyr Val Ser
                165                 170                 175

Trp Tyr Gln Arg His Pro Gly Lys Ala Pro Lys Leu Ile Ile Tyr Asp
            180                 185                 190

Val Ser Glu Arg Pro Ser Gly Val Ser Asn Arg Phe Ser Gly Ser Lys
        195                 200                 205

Ser Gly Asn Thr Ala Ser Leu Thr Ile Ser Gly Leu Gln Ala Glu Asp
    210                 215                 220

Glu Ala Asp Tyr Tyr Cys Ser Ser Tyr Thr Thr Arg Thr Thr Gln Ala
225                 230                 235                 240

Val Phe Gly Gly Gly Thr Gln Leu Thr Val Leu Ser Gly Ile Leu Glu
                245                 250                 255

Gln Lys Leu Ile Ser Glu Glu Asp
            260

<210> SEQ ID NO 11
<211> LENGTH: 267
<212> TYPE: PRT
<213> ORGANISM: Homo sapiens

<400> SEQUENCE: 11

Ala Ser Glu Val Gln Leu Gln Gln Ser Gly Pro Gly Leu Val Lys Pro
1               5                   10                  15

Ser Gln Thr Leu Ser Leu Thr Cys Asp Ile Ser Gly Asp Ser Val Ser
            20                  25                  30

Ser Asn Ser Ala Ala Trp Asn Trp Ile Arg Gln Ser Pro Ser Arg Gly
        35                  40                  45

Leu Glu Trp Leu Gly Arg Thr Tyr Tyr Arg Ser Lys Trp Tyr Asn Asp
    50                  55                  60

Tyr Ala Val Ser Val Lys Ser Arg Ile Thr Ile Asn Pro Asp Thr Ser
65                  70                  75                  80

Lys Asn Gln Phe Ser Leu His Leu Asn Ser Val Thr Pro Glu Asp Thr
                85                  90                  95

Ala Val Tyr Tyr Cys Ala Arg Ala Asn Thr Arg Gly Tyr Phe Asp Leu
            100                 105                 110

Trp Gly Arg Gly Thr Leu Val Thr Val Ser Ser Gly Ile Leu Gly Ser
        115                 120                 125

Gly Gly Gly Gly Ser Gly Gly Gly Ser Gly Gly Gly Gly Ser Gln
    130                 135                 140

Pro Val Leu Thr Gln Ser Pro Ser Ala Ser Gly Thr Pro Gly Gln Arg
145                 150                 155                 160

Val Thr Ile Ser Cys Ser Gly Gly Ser Ser Asn Ile Gly Ser Arg Tyr
                165                 170                 175

Val Tyr Trp Tyr Gln Gln Leu Pro Gly Thr Ala Pro Lys Leu Leu Ile
            180                 185                 190

Tyr Lys Asn Asn Gln Arg Pro Ser Gly Val Pro Asp Arg Phe Ser Gly
        195                 200                 205

Ser Lys Ser Gly Thr Ser Ala Ser Leu Ala Ile Ser Gly Leu Arg Ser
    210                 215                 220

Glu Asp Glu Ala Asp Tyr Tyr Cys Ala Ala Trp Asp Asp Ile Leu Ser
```

```
                 225                 230                 235                 240
Gly Thr Val Phe Gly Gly Gly Thr Gln Leu Thr Val Leu Ser Gly Ile
                245                 250                 255

Leu Glu Gln Lys Leu Ile Ser Glu Glu Asp Leu
            260                 265

<210> SEQ ID NO 12
<211> LENGTH: 267
<212> TYPE: PRT
<213> ORGANISM: Homo sapiens

<400> SEQUENCE: 12

Ala Ser Gln Val Gln Leu Gln Gln Ser Gly Lys Asp Trp Arg Ser Pro
1               5                   10                  15

Arg Arg Arg Ser His Ser Pro Asp Asp Ile Ser Gly Asp Ser Val Ser
            20                  25                  30

Ser Asn Ser Ala Ala Trp Asn Trp Ile Arg Gln Ser Pro Ser Arg Gly
        35                  40                  45

Leu Glu Trp Leu Gly Arg Thr Tyr Tyr Arg Ser Lys Trp Tyr Asn Asp
    50                  55                  60

Tyr Ala Val Ser Val Lys Ser Arg Ile Thr Ile Asn Pro Asp Thr Ser
65                  70                  75                  80

Lys Asn Gln Phe Ser Leu His Leu Asn Ser Val Thr Pro Glu Asp Thr
                85                  90                  95

Ala Val Tyr Tyr Cys Ala Arg Ala Asn Thr Arg Gly Tyr Phe Asp Leu
            100                 105                 110

Trp Gly Arg Gly Thr Leu Val Thr Val Ser Ser Gly Ile Leu Gly Ser
        115                 120                 125

Gly Gly Gly Gly Ser Gly Gly Gly Gly Ser Gly Gly Gly Gly Ser Gln
    130                 135                 140

Pro Val Leu Thr Gln Ser Pro Ser Ala Ser Gly Thr Pro Gly Gln Arg
145                 150                 155                 160

Val Thr Ile Ser Cys Ser Gly Gly Ser Ser Asn Ile Gly Ser Arg Tyr
                165                 170                 175

Val Tyr Trp Tyr Gln Gln Leu Pro Gly Thr Ala Pro Lys Leu Leu Ile
            180                 185                 190

Tyr Lys Asn Asn Gln Arg Pro Ser Gly Val Pro Asp Arg Phe Ser Gly
        195                 200                 205

Ser Lys Ser Gly Thr Ser Ala Ser Leu Ala Ile Ser Gly Leu Arg Thr
    210                 215                 220

Glu Asp Glu Ala Asp Tyr Tyr Cys Ala Ala Trp Asp Asp Ile Leu Ser
225                 230                 235                 240

Gly Thr Val Phe Gly Gly Ala Ser Gln Leu Thr Val Leu Ser Gly Ile
                245                 250                 255

Leu Glu Gln Lys Leu Ile Ser Glu Glu Asp Leu
            260                 265

<210> SEQ ID NO 13
<211> LENGTH: 266
<212> TYPE: PRT
<213> ORGANISM: Homo sapiens

<400> SEQUENCE: 13

Ala Ser Gln Val Gln Leu Gln Gln Ser Gly Pro Gly Leu Val Lys Pro
1               5                   10                  15

Ser Gln Thr Leu Ser Leu Thr Cys Val Ile Ser Gly Asp Ser Val Ser
```

```
                    20                  25                  30
Asn Ser Ser Ala Ala Trp Asn Trp Ile Arg Gln Ser Pro Ser Arg Gly
            35                  40                  45

Leu Glu Trp Leu Gly Arg Thr Tyr Tyr Arg Ser Lys Trp Tyr Asn Asp
 50                  55                  60

Tyr Ala Glu Ser Val Lys Ser Arg Ile Thr Ile Asn Pro Asp Thr Ser
 65                  70                  75                  80

Lys Asn Gln Phe Ser Leu Gln Leu Asn Ser Val Thr Pro Glu Asp Thr
                 85                  90                  95

Ala Val Tyr Tyr Cys Ala Arg Ser Arg Leu Gly His Phe Asp Ser Trp
                100                 105                 110

Gly Gln Gly Thr Leu Val Thr Val Ser Ser Gly Ile Leu Gly Ser Gly
                115                 120                 125

Gly Gly Gly Ser Gly Gly Gly Ser Gly Gly Gly Ser Ser Tyr
                130                 135                 140

Glu Leu Thr Gln Pro Pro Ser Ala Ser Gly Thr Pro Gly Gln Arg Val
145                 150                 155                 160

Thr Ile Ser Cys Ser Gly Gly Ser Ser Asn Ile Gly Ser Arg Tyr Val
                165                 170                 175

Tyr Trp Tyr Gln Gln Leu Pro Gly Thr Ala Pro Lys Leu Leu Ile Tyr
                180                 185                 190

Lys Asn Asn Gln Arg Pro Ser Gly Val Pro Asp Arg Phe Ser Gly Ser
                195                 200                 205

Lys Ser Gly Thr Ser Ala Ser Leu Ala Ile Ser Gly Leu Arg Ser Glu
                210                 215                 220

Asp Glu Ala Asp Tyr Tyr Cys Ala Ala Trp Asp Asp Ile Leu Ser Gly
225                 230                 235                 240

Thr Val Phe Gly Gly Gly Thr Gln Leu Thr Val Leu Ser Gly Ile Leu
                245                 250                 255

Glu Gln Lys Leu Ile Ser Glu Glu Asp Leu
                260                 265

<210> SEQ ID NO 14
<211> LENGTH: 150
<212> TYPE: PRT
<213> ORGANISM: Homo sapiens

<400> SEQUENCE: 14

Ala Ser Glu Val Gln Leu Leu Glu Thr Gly Gly Gly Leu Val Lys Pro
 1                   5                  10                  15

Gly Gly Ser Arg Arg Leu Ser Cys Ala Ala Ser Gly Phe Thr Phe Ser
                20                  25                  30

Asn Ala Trp Met Ser Trp Val Arg Gln Ala Pro Gly Lys Gly Leu Glu
            35                  40                  45

Trp Val Gly Arg Val Lys Ser Lys Thr Asp Gly Thr Thr Asp Tyr
 50                  55                  60

Ala Ala Pro Val Lys Gly Arg Phe Thr Ile Ser Arg Asp Asp Ser Lys
 65                  70                  75                  80

Asn Thr Leu Tyr Leu Gln Met Asn Ser Leu Lys Thr Glu Asp Thr Ala
                 85                  90                  95

Val Tyr Tyr Cys Thr Thr Glu Tyr Tyr Ser Asp Ser Ser Gly Asp Tyr
                100                 105                 110

Trp Gly Arg Tyr Trp Gly Gln Gly Thr Leu Val Thr Val Ser Ser Gly
                115                 120                 125
```

```
Ile Leu Gly Ser Gly Gly Gly Ser Gly Gly Gly Ser Gly Gly
    130                 135                 140

Gly Gly Leu Gln Glu Phe
145                 150

<210> SEQ ID NO 15
<211> LENGTH: 152
<212> TYPE: PRT
<213> ORGANISM: Homo sapiens

<400> SEQUENCE: 15

Ala Ser Gln Val Gln Leu Val Lys Ser Glu Gly Gly Val Val Gln Pro
1               5                   10                  15

Gly Arg Ser Leu Arg Leu Ser Cys Ala Ala Ser Gly Phe Thr Phe Ser
            20                  25                  30

Ser Tyr Ala Met His Trp Val Arg Gln Ala Pro Gly Lys Gly Leu Glu
        35                  40                  45

Trp Val Ala Val Ile Ser Tyr Asp Gly Ser Asn Lys Tyr Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Asp Asp Thr Ala Val Tyr
                85                  90                  95

Tyr Cys Ala Arg Gly Arg Leu Lys Asn Asp Asp Tyr Gly Asp Tyr Trp
            100                 105                 110

Gly Gln Gly Thr Leu Val Thr Val Ser Ser Gly Ser Ala Ser Ala Pro
        115                 120                 125

Thr Gly Ile Leu Gly Ser Gly Gly Gly Ser Gly Gly Gly Gly Ser
    130                 135                 140

Gly Gly Gly Gly Leu Gln Glu Phe
145                 150

<210> SEQ ID NO 16
<211> LENGTH: 164
<212> TYPE: PRT
<213> ORGANISM: Homo sapiens

<400> SEQUENCE: 16

Arg Tyr Pro Tyr Asp Val Pro Asp Tyr Ala Leu Gln Ala Ser Gly Gly
1               5                   10                  15

Gly Gly Ser Gly Gly Gly Gly Ser Gly Gly Gly Gly Ser Ala Ser Glu
            20                  25                  30

Val Gln Leu Val Glu Ser Gly Gly Gly Ser Val Gln Pro Gly Gly Ser
        35                  40                  45

Leu Arg Leu Ser Cys Ala Ala Ser Gly Phe Thr Phe Ser Ser Tyr Pro
    50                  55                  60

Met His Trp Val Arg Leu Ala Pro Gly Lys Gly Leu Glu Trp Val Ala
65                  70                  75                  80

Leu Thr Ser Tyr Asp Gly Gly Asp Lys Tyr Tyr Ala Asp Ser Val Lys
                85                  90                  95

Gly Arg Phe Thr Ile Ser Arg Asp Asn Ser Lys Asn Ala Leu Tyr Leu
            100                 105                 110

Gln Met Asn Ser Leu Arg Thr Glu Asp Thr Ala Ile Tyr Tyr Cys Ala
        115                 120                 125

Arg His Gly Tyr Thr Ser Gly Trp Leu Arg Asn Trp Gly Gln Gly Thr
    130                 135                 140
```

```
Leu Val Thr Val Ser Ser Gly Ile Leu Gly Ser Gly Gly Gly Ser
145                 150                 155                 160

Gly Gly Gly Gly

<210> SEQ ID NO 17
<211> LENGTH: 263
<212> TYPE: PRT
<213> ORGANISM: Homo sapiens

<400> SEQUENCE: 17

Ala Ser Glu Val Gln Leu Val Glu Ser Gly Gly Gly Leu Val Gln Pro
1               5                   10                  15

Gly Gly Ser Leu Arg Leu Ser Cys Ala Thr Ser Gly Phe Thr Phe Ser
                20                  25                  30

Asp Asp Trp Met Thr Trp Val Arg Gln Ala Pro Gly Lys Gly Leu Glu
            35                  40                  45

Trp Val Ala Asn Ile Lys Gln Asp Gly Ser Glu Lys Tyr Tyr Ala Asp
        50                  55                  60

Ser Val Lys Gly Arg Phe Thr Ile Ser Arg Asp Asn Ala Lys Asn Ser
65                  70                  75                  80

Leu Tyr Leu Gln Met Asn Ile Leu Arg Ala Asp Asp Ser Ala Val Tyr
                85                  90                  95

Tyr Cys Ala Arg Gly Arg Trp Gly Leu Asp Val Trp Gly Gln Gly Thr
            100                 105                 110

Thr Val Thr Val Ser Ser Gly Ile Leu Gly Ser Gly Gly Gly Gly Ser
        115                 120                 125

Gly Gly Gly Gly Ser Gly Gly Gly Ser Asn Phe Met Leu Thr Gln
130                 135                 140

Pro His Ser Val Ser Glu Ser Pro Gly Lys Thr Val Thr Ile Ser Cys
145                 150                 155                 160

Thr Gly Ser Ser Gly Ser Ile Ala Ser Asn Tyr Val Gln Trp Tyr Gln
                165                 170                 175

Gln Arg Pro Gly Ser Ala Pro Thr Thr Val Ile Tyr Glu Asp Asn Gln
            180                 185                 190

Arg Pro Ser Gly Val Pro Asp Arg Phe Ser Gly Ser Ile Asp Arg Ser
        195                 200                 205

Ser Asn Ser Ala Ser Leu Thr Ile Ser Gly Leu Lys Thr Glu Asp Glu
    210                 215                 220

Ala Asp Tyr Tyr Cys Gln Ser Tyr Asp Ser Asn His Ala Val Phe
225                 230                 235                 240

Gly Gly Gly Thr Pro Ala Asp Arg Pro Leu Arg Ile Leu Glu Gln Lys
                245                 250                 255

Leu Ile Ser Glu Glu Asp Leu
            260

<210> SEQ ID NO 18
<211> LENGTH: 255
<212> TYPE: PRT
<213> ORGANISM: Homo sapiens

<400> SEQUENCE: 18

Ala Ser Gln Val Gln Leu Gln Glu Ser Gly Pro Gly Leu Val Lys Pro
1               5                   10                  15

Ser Gln Thr Leu Ser Leu Thr Cys Thr Val Ser Gly Gly Ser Ile Ser
                20                  25                  30

Asn Gly Trp Tyr Tyr Trp Ser Trp Ile Arg Gln Pro Ala Gly Lys Gly
```

-continued

```
                35                  40                  45
Leu Glu Trp Ile Gly His Ile His Thr Ser Gly Ser Thr Lys Phe Asn
 50                  55                  60
Pro Ser Leu Lys Ser Arg Ile Thr Met Ser Val Asp Thr Ser Thr Asn
65                  70                  75                  80
Gln Phe Ser Leu Asn Leu Ser Ser Val Thr Ala Ala Asp Thr Ala Val
                85                  90                  95
Tyr Tyr Cys Ala Arg Phe Asp Trp Ser Ala Tyr Ser Ser Ala Phe Asp
            100                 105                 110
Tyr Trp Gly Gln Gly Thr Leu Val Thr Val Ser Ser Gly Ile Leu Gly
            115                 120                 125
Ser Gly Gly Gly Gly Ser Gly Gly Gly Gly Ser Gly Gly Gly Gly Ser
        130                 135                 140
Asn Phe Met Leu Thr Gln Pro His Ser Val Ser Glu Ser Pro Gly Lys
145                 150                 155                 160
Thr Val Thr Ile Ser Cys Thr Gly Ser Ser Gly Ser Ile Ala Ser Asn
                165                 170                 175
Tyr Val Gln Trp Tyr Gln Gln Arg Pro Gly Ser Ala Pro Thr Thr Val
            180                 185                 190
Ile Tyr Glu Asp Asp Gln Arg Pro Ser Gly Val Pro Asp Arg Phe Ser
            195                 200                 205
Gly Ser Ile Asp Ser Ser Ser Asn Ser Ala Ser Leu Thr Ile Ser Gly
        210                 215                 220
Leu Lys Thr Glu Asp Glu Ala Asp Tyr Tyr Cys Gln Ser Tyr Asp Ser
225                 230                 235                 240
Asn Asn Phe Val Val Phe Gly Gly Gly Asn Gln Leu Thr Val Phe
                245                 250                 255

<210> SEQ ID NO 19
<211> LENGTH: 266
<212> TYPE: PRT
<213> ORGANISM: Homo sapiens

<400> SEQUENCE: 19

Ala Ser Gln Val Gln Leu Gln Glu Ser Gly Pro Gly Leu Val Lys Pro
1               5                  10                  15
Ser Gln Thr Leu Ser Leu Thr Cys Thr Val Ser Gly Gly Ser Ile Ser
                20                  25                  30
Asn Gly Trp Tyr Tyr Trp Ser Trp Ile Arg Gln Pro Ala Gly Lys Gly
            35                  40                  45
Leu Glu Trp Ile Gly His Ile His Thr Ser Gly Ser Thr Lys Phe Asn
 50                  55                  60
Pro Ser Leu Lys Ser Arg Ile Thr Met Ser Val Asp Thr Ser Thr Asn
65                  70                  75                  80
Gln Phe Ser Leu Asn Leu Ser Ser Val Thr Ala Ala Asp Thr Ala Val
                85                  90                  95
Tyr Tyr Cys Ala Arg Phe Asp Trp Ser Ala Tyr Ser Ser Ala Phe Asp
            100                 105                 110
Tyr Trp Gly Gln Gly Thr Leu Val Thr Val Ser Ser Gly Ile Leu Gly
            115                 120                 125
Ser Gly Gly Gly Gly Ser Gly Gly Gly Gly Ser Gly Gly Gly Gly Ser
        130                 135                 140
Asn Phe Met Leu Thr Gln Pro His Ser Val Ser Glu Ser Pro Gly Lys
145                 150                 155                 160
```

```
Thr Val Thr Ile Ser Cys Thr Gly Ser Gly Ser Ile Ala Ser Asn
                165                 170                 175

Tyr Val Gln Trp Tyr Gln Gln Arg Pro Gly Ser Ala Pro Thr Thr Val
            180                 185                 190

Ile Tyr Glu Asp Asp Gln Arg Pro Ser Gly Val Pro Asp Arg Phe Ser
        195                 200                 205

Gly Ser Ile Asp Ser Ser Ser Asn Ser Ala Ser Leu Thr Ile Ser Gly
    210                 215                 220

Leu Lys Thr Glu Asp Glu Ala Asp Tyr Tyr Cys Gln Ser Tyr Asp Ser
225                 230                 235                 240

Asn Asn Phe Val Val Phe Gly Gly Gly Thr Gln Leu Thr Val Leu Ser
                245                 250                 255

Gly Ile Leu Glu Gln Lys Leu Ile Ser Glu
            260                 265

<210> SEQ ID NO 20
<211> LENGTH: 257
<212> TYPE: PRT
<213> ORGANISM: Homo sapiens

<400> SEQUENCE: 20

Ala Ser Gln Val Gln Leu Gln Gln Trp Gly Ala Gly Leu Leu Lys Pro
1               5                   10                  15

Ser Glu Thr Leu Ser Leu Thr Cys Ala Ile Ser Gly Asp Thr Val Ser
            20                  25                  30

Ser His Ser Ala Lys Trp Asn Trp Phe Arg Gln Ser Pro Ser Arg Gly
        35                  40                  45

Leu Glu Trp Leu Gly Arg Thr Tyr Tyr Arg Ser Lys Trp Tyr Asn Asp
    50                  55                  60

Tyr Ala Leu Ser Val Lys Ser Arg Ile Thr Ile Asn Pro Asp Thr Ala
65                  70                  75                  80

Lys Asn Gln Phe Ser Leu Gln Leu Ser Ser Val Thr Pro Glu Asp Thr
                85                  90                  95

Ala Val Tyr Phe Cys Ala Arg Gln Val Arg Gly Trp Gln Asn Trp His
            100                 105                 110

Phe Asp Leu Trp Gly Arg Gly Thr Leu Val Thr Val Ser Ser Gly Ile
        115                 120                 125

Leu Gly Ser Gly Gly Gly Gly Ser Gly Gly Gly Ser Gly Gly Gly
    130                 135                 140

Gly Ser Gln Pro Val Leu Thr Gln Ser Pro Ser Ala Ser Gly Thr Pro
145                 150                 155                 160

Gly Gln Arg Val Thr Ile Ser Cys Ser Gly Ser Ser Asn Ile Gly
                165                 170                 175

Ser Asn Thr Val Asn Trp Tyr Gln Gln Leu Pro Gly Thr Ala Pro Lys
            180                 185                 190

Leu Leu Ile Tyr Ser Asn Asn Gln Arg Pro Ser Gly Val Pro Asp Arg
        195                 200                 205

Phe Ser Gly Ser Lys Ser Gly Thr Ser Ala Ser Leu Ala Ile Ser Gly
    210                 215                 220

Leu Gln Ser Glu Asp Glu Ala Asp Tyr Tyr Cys Ala Ala Trp Asp Asp
225                 230                 235                 240

Arg Phe Lys Gly Tyr Val Phe Gly Gly Gly Thr Lys Leu Thr Arg Pro
                245                 250                 255

Ile
```

```
<210> SEQ ID NO 21
<211> LENGTH: 246
<212> TYPE: PRT
<213> ORGANISM: Homo sapiens

<400> SEQUENCE: 21

Ala Ser Gln Leu Gln Leu Gln Gln Ser Gly Pro Gly Leu Val Lys Ala
1               5                   10                  15

Leu Ala Asp Pro Leu Thr His Cys Ala Ile Ser Gly Asp Ser Val Ser
            20                  25                  30

Ser Asn Ser Ala Thr Trp Asn Trp Ile Arg Gln Ser Pro Ser Arg Gly
        35                  40                  45

Leu Glu Trp Leu Gly Arg Thr Tyr Tyr Arg Ser Lys Trp Ser Asn Asp
    50                  55                  60

Tyr Ala Gly Ser Val Lys Ser Arg Ile Thr Ile Asn Ala Asp Thr Ser
65                  70                  75                  80

Lys Asn Gln Phe Ser Leu Gln Leu Asn Ser Val Thr Pro Glu Asp Thr
                85                  90                  95

Ala Val Tyr Tyr Cys Ala Arg Gly Asp Gly Ser Ser Gly Trp Ser Gly
            100                 105                 110

Val Asn Ala Phe Asp Ile Trp Gly Gln Gly Thr Met Val Thr Val Ser
        115                 120                 125

Ser Gly Ile Leu Gly Ser Gly Gly Gly Ser Gly Gly Gly Gly Ser
    130                 135                 140

Gly Gly Gly Gly Ser Gln Ser Ala Leu Thr Gln Pro Ala Ser Val Ser
145                 150                 155                 160

Gly Ser Pro Gly Gln Ser Ile Thr Ile Ser Cys Thr Gly Thr Ser Ser
                165                 170                 175

Asp Val Gly Ser Tyr Asn Leu Val Ser Trp Tyr Gln Gln His Pro Gly
            180                 185                 190

Lys Ala Pro Lys Leu Met Ile Tyr Glu Val Ser Lys Arg Pro Ser Gly
        195                 200                 205

Val Ser Asn Arg Phe Ser Gly Ser Lys Ser Gly Asn Thr Ala Ser Leu
    210                 215                 220

Thr Ile Ser Gly Leu Gln Ala Glu Asp Glu Ala Asp Tyr Tyr Cys Ala
225                 230                 235                 240

His Thr Gln Val Ala Ala
                245

<210> SEQ ID NO 22
<211> LENGTH: 242
<212> TYPE: PRT
<213> ORGANISM: Homo sapiens

<400> SEQUENCE: 22

Ala Ser Gln Val Gln Leu Gln Gln Ser Gly Pro Gly Leu Val Lys Pro
1               5                   10                  15

Arg Arg Pro Ser His Ser Pro Val Pro Ser Pro Gly Thr Val Ser Leu
            20                  25                  30

Ala Thr Val Leu Leu Gly Asn Trp Ile Arg Gln Ser Pro Ser Arg Gly
        35                  40                  45

Leu Glu Trp Leu Gly Arg Thr Tyr Tyr Arg Ser Lys Trp Ser Asn Asp
    50                  55                  60

Tyr Ala Gly Ser Val Lys Ser Arg Ile Thr Ile Asn Ala Asp Thr Ser
65                  70                  75                  80
```

-continued

```
Lys Asn Gln Phe Ser Leu Gln Leu Asn Ser Val Thr Pro Glu Asp Thr
                 85                  90                  95

Ala Val Tyr Tyr Cys Ala Arg Gly Asp Gly Ser Ser Gly Trp Ser Gly
            100                 105                 110

Val Asn Ala Phe Asp Ile Trp Gly Gln Gly Thr Met Val Thr Val Ser
        115                 120                 125

Ser Gly Ile Leu Gly Ser Gly Gly Gly Ser Gly Gly Gly Gly Ser
    130                 135                 140

Gly Gly Gly Gly Ser Gln Ser Ala Leu Thr Gln Pro Ala Ser Val Ser
145                 150                 155                 160

Gly Ser Pro Gly Gln Ser Ile Thr Ile Ser Cys Thr Gly Thr Ser Ser
                165                 170                 175

Asp Val Gly Ser Tyr Asn Leu Val Ser Trp Tyr Gln Gln His Pro Gly
            180                 185                 190

Lys Ala Pro Lys Leu Met Ile Tyr Glu Val Ser Lys Arg Pro Ser Gly
        195                 200                 205

Val Ser Asn Arg Phe Ser Gly Ser Lys Ser Gly Asn Thr Ala Ser Leu
    210                 215                 220

Thr Ile Ser Gly Leu Gln Ala Glu Asp Glu Ala Asp Tyr Tyr Cys Cys
225                 230                 235                 240

Ser His

<210> SEQ ID NO 23
<211> LENGTH: 273
<212> TYPE: PRT
<213> ORGANISM: Homo sapiens

<400> SEQUENCE: 23

Ala Ser Gln Val Gln Leu Gln Gln Ser Gly Pro Gly Leu Val Lys Pro
1               5                   10                  15

Ser Gln Thr Leu Ser Leu Thr Cys Ala Ile Ser Gly Asp Ser Val Ser
            20                  25                  30

Ser Asn Ser Ala Thr Trp Asn Trp Ile Arg Gln Ser Pro Ser Arg Gly
        35                  40                  45

Leu Glu Trp Leu Gly Arg Thr Tyr Tyr Arg Ser Lys Trp Ser Asn Asp
    50                  55                  60

Tyr Ala Gly Ser Val Lys Ser Arg Ile Thr Ile Asn Ala Asp Thr Ser
65                  70                  75                  80

Lys Asn Gln Phe Ser Leu Gln Leu Asn Ser Val Thr Pro Glu Asp Thr
                85                  90                  95

Ala Val Tyr Tyr Cys Ala Arg Gly Asp Gly Ser Ser Gly Trp Ser Gly
            100                 105                 110

Val Asn Ala Phe Asp Ile Trp Gly Gln Gly Thr Met Val Thr Val Ser
        115                 120                 125

Ser Gly Ile Leu Gly Ser Gly Gly Gly Ser Gly Gly Gly Gly Ser
    130                 135                 140

Gly Gly Gly Gly Ser Gln Ser Ala Leu Thr Gln Pro Ala Ser Val Ser
145                 150                 155                 160

Gly Ser Pro Gly Gln Ser Ile Thr Ile Ser Cys Thr Gly Thr Ser Ser
                165                 170                 175

Asp Val Gly Ser Tyr Asn Leu Val Ser Trp Tyr Gln Gln His Pro Gly
            180                 185                 190

Lys Ala Pro Lys Leu Met Ile Tyr Glu Val Ser Lys Arg Pro Ser Gly
        195                 200                 205
```

```
Val Ser Asn Arg Phe Ser Gly Ser Lys Ser Gly Asn Thr Ala Ser Leu
    210                 215                 220

Thr Ile Ser Gly Leu Gln Ala Glu Asp Glu Ala Asp Tyr Tyr Cys Cys
225                 230                 235                 240

Ser Tyr Ala Gly Ser Gly Thr Leu Val Phe Gly Gly Gly Thr Lys Leu
                245                 250                 255

Thr Val Leu Ser Gly Ile Leu Glu Gln Lys Leu Ile Ser Glu Glu Asp
            260                 265                 270

Leu
```

```
<210> SEQ ID NO 24
<211> LENGTH: 277
<212> TYPE: PRT
<213> ORGANISM: Homo sapiens

<400> SEQUENCE: 24
```

```
Gly Gly Gly Ser Ala Ser Gln Val Gln Leu Gln Gln Ser Gly Pro Gly
1               5                   10                  15

Leu Val Lys Pro Ser Gln Thr Leu Ser Leu Thr Cys Ala Ile Ser Gly
            20                  25                  30

Asp Ser Val Ser Ser Asn Ser Ala Thr Trp Asn Trp Ile Arg Gln Ser
        35                  40                  45

Pro Ser Arg Gly Leu Glu Trp Leu Gly Arg Thr Tyr Tyr Arg Ser Lys
    50                  55                  60

Trp Ser Asn Asp Tyr Ala Gly Ser Val Lys Ser Arg Ile Thr Ile Asn
65                  70                  75                  80

Ala Asp Thr Ser Lys Asn Gln Phe Ser Leu Gln Leu Asn Ser Val Thr
                85                  90                  95

Pro Glu Asp Thr Ala Val Tyr Tyr Cys Ala Arg Gly Asp Gly Ser Ser
            100                 105                 110

Gly Trp Ser Gly Val Asn Ala Phe Asp Ile Trp Gly Gln Gly Thr Met
        115                 120                 125

Val Thr Val Ser Ser Gly Ile Leu Gly Ser Gly Gly Gly Gly Ser Gly
    130                 135                 140

Gly Gly Gly Ser Gly Gly Gly Ser Gln Ser Ala Leu Thr Gln Pro
145                 150                 155                 160

Ala Ser Val Ser Gly Ser Pro Gly Gln Ser Ile Thr Ile Ser Cys Thr
                165                 170                 175

Gly Thr Ser Ser Asp Val Gly Ser Tyr Asn Leu Val Ser Trp Tyr Gln
            180                 185                 190

Gln His Pro Gly Lys Ala Pro Lys Leu Met Ile Tyr Glu Val Ser Lys
        195                 200                 205

Arg Pro Ser Gly Val Ser Asn Arg Phe Ser Gly Ser Lys Ser Gly Asn
    210                 215                 220

Thr Ala Ser Leu Thr Ile Ser Gly Leu Gln Ala Glu Asp Glu Ala Asp
225                 230                 235                 240

Tyr Tyr Cys Cys Ser Tyr Ala Gly Ser Gly Thr Leu Val Phe Gly Gly
                245                 250                 255

Arg Thr Lys Leu Thr Val Leu Ser Gly Ile Leu Glu Gln Lys Leu Ile
            260                 265                 270

Ser Glu Glu Asp Leu
                275
```

```
<210> SEQ ID NO 25
<211> LENGTH: 268
```

<212> TYPE: PRT
<213> ORGANISM: Homo sapiens

<400> SEQUENCE: 25

```
Ala Ser Gln Val Gln Leu Gln Gln Ser Gly Pro Gly Leu Val Lys Pro
1               5                   10                  15

Ser Gln Ser Leu Ser Leu Thr Cys Ala Ile Ser Gly Asp Ser Val Ser
            20                  25                  30

Ser Asn Ser Ala Thr Trp Asn Trp Ile Arg Gln Ser Pro Ser Arg Gly
        35                  40                  45

Leu Glu Trp Leu Gly Arg Thr Tyr Tyr Arg Ser Lys Trp Ser Asn Asp
50                  55                  60

Tyr Ala Gly Ser Val Lys Ser Arg Ile Thr Ile Asn Ala Asp Thr Ser
65                  70                  75                  80

Lys Asn Gln Phe Ser Leu Gln Leu Asn Ser Val Thr Pro Glu Asp Thr
                85                  90                  95

Ala Val Tyr Tyr Cys Ala Arg Gly Asp Gly Ser Ser Gly Trp Ser Gly
            100                 105                 110

Val Asn Ala Phe Asp Ile Arg Gly Gln Gly Thr Met Val Thr Val Ser
        115                 120                 125

Ser Gly Ile Leu Gly Ser Gly Gly Gly Ser Gly Gly Gly Gly Gly Ser
130                 135                 140

Gly Gly Gly Gly Ser Gln Ser Ala Leu Thr Gln Pro Ala Ser Val Ser
145                 150                 155                 160

Gly Ser Pro Gly Gln Ser Ile Thr Ile Ser Cys Thr Gly Thr Ser Ser
                165                 170                 175

Asp Val Gly Ser Tyr Asn Leu Val Ser Trp Tyr Gln Gln His Pro Gly
            180                 185                 190

Lys Ala Pro Lys Leu Met Ile Tyr Glu Val Ser Lys Arg Pro Ser Gly
        195                 200                 205

Val Ser Asn Arg Phe Ser Gly Ser Lys Ser Gly Asn Thr Ala Ser Leu
    210                 215                 220

Thr Ile Ser Gly Leu Gln Ala Glu Asp Glu Ala Asp Tyr Tyr Cys Cys
225                 230                 235                 240

Ser Tyr Ala Gly Ser Gly Thr Leu Val Phe Gly Gly Gly Thr Lys Leu
                245                 250                 255

Thr Val Leu Ser Gly Ile Leu Glu Gln Lys Leu Ile
            260                 265
```

<210> SEQ ID NO 26
<211> LENGTH: 264
<212> TYPE: PRT
<213> ORGANISM: Homo sapiens

<400> SEQUENCE: 26

```
Ala Ser Gln Ala Ala Trp Cys Arg Ser Gly Ala Glu Val Lys Lys Pro
1               5                   10                  15

Gly Ala Ser Met Lys Val Ser Cys Lys Ala Ser Gly Tyr Thr Phe Ser
            20                  25                  30

Ser His Gly Ile Ser Trp Val Arg Gln Ala Pro Gly Gln Arg Leu Glu
        35                  40                  45

Trp Met Gly Trp Ile Asn Ala Gly Asn Gly His Thr Arg Tyr Ser Gln
50                  55                  60

Lys Phe Gln Gly Arg Val Thr Ile Thr Arg Asp Thr Ser Ala Arg Met
65                  70                  75                  80
```

Asp Tyr Met Asp Leu Ser Ser Leu Thr Ser Asp Asp Thr Ala Val Tyr
                85                  90                  95

Tyr Cys Ala Arg Gly Gly Gly Thr His Gly Phe Asp Tyr Trp Gly Gln
            100                 105                 110

Gly Thr Leu Val Thr Ala Ser Ser Ala Ser Thr Lys Gly Pro Ser Gly
        115                 120                 125

Ile Leu Gly Ser Gly Gly Gly Gly Ser Gly Gly Gly Gly Ser Gly Gly
    130                 135                 140

Gly Gly Ser Glu Ile Val Leu Thr Gln Ser Pro Gly Thr Leu Ser Leu
145                 150                 155                 160

Ser Pro Gly Asp Gly Ala Thr Leu Ser Cys Arg Ala Ser Gln Ser Val
                165                 170                 175

Ser Ser Asn Tyr Leu Ala Trp Tyr Gln Gln Ile Pro Gly Gln Ala Pro
            180                 185                 190

Arg Leu Leu Ile His Gly Ala Ser Thr Arg Ala Ser Gly Ile Pro Asp
        195                 200                 205

Arg Phe Arg Gly Ser Ala Ser Gly Thr Asp Phe Thr Leu Thr Ile Ser
    210                 215                 220

Arg Leu Glu Pro Glu Asp Phe Ala Leu Tyr Tyr Cys Gln Gln Tyr Gly
225                 230                 235                 240

Arg Ser Pro Ile Thr Phe Gly Pro Arg Asp Asn Asp Trp Arg Leu Asn
                245                 250                 255

Pro Glu Phe Leu Glu Gln Lys Leu
            260

<210> SEQ ID NO 27
<211> LENGTH: 259
<212> TYPE: PRT
<213> ORGANISM: Homo sapiens

<400> SEQUENCE: 27

Ala Ser Gln Val Gln Leu Val Gln Ser Gly Ala Glu Val Lys Lys Pro
1               5                   10                  15

Gly Ala Ser Val Lys Val Ser Cys Lys Ala Ser Gly Tyr Thr Phe Ser
            20                  25                  30

Ser His Gly Ile Ser Trp Val Arg Gln Ala Pro Gly Gln Arg Leu Glu
        35                  40                  45

Trp Met Gly Trp Ile Asn Ala Gly Asn Gly His Thr Arg Tyr Ser Gln
    50                  55                  60

Lys Phe Gln Gly Arg Val Thr Ile Thr Arg Asp Thr Ser Ala Arg Met
65                  70                  75                  80

Ala Tyr Met Asp Leu Ser Ser Leu Thr Ser Asp Asp Thr Ala Val Tyr
                85                  90                  95

Tyr Cys Ala Arg Gly Gly Gly Thr His Gly Phe Asp Tyr Trp Gly Gln
            100                 105                 110

Gly Thr Leu Val Thr Ala Ser Ser Ala Ser Thr Lys Gly Pro Ser Gly
        115                 120                 125

Ile Leu Gly Ser Gly Gly Gly Gly Ser Gly Gly Gly Gly Ser Gly Gly
    130                 135                 140

Gly Gly Ser Glu Ile Val Leu Thr Gln Ser Pro Gly Thr Leu Ser Leu
145                 150                 155                 160

Ser Pro Gly Asp Gly Ala Thr Leu Ser Cys Arg Ala Ser Gln Ser Val
                165                 170                 175

Ser Ser Asn Tyr Leu Ala Trp Tyr Gln Gln Ile Pro Gly Gln Ala Pro
            180                 185                 190

```
Arg Leu Leu Ile His Gly Ala Ser Thr Arg Ala Ser Gly Ile Pro Asp
            195                 200                 205

Arg Phe Arg Gly Ser Ala Ser Gly Thr Asp Phe Thr Leu Thr Ile Ser
        210                 215                 220

Arg Leu Glu Pro Glu Asp Phe Ala Leu Tyr Tyr Cys Gly Gln Tyr Gly
225                 230                 235                 240

Arg Ser Pro Ile Thr Phe Gly Gln Gly Thr Thr Ser Trp Arg Leu Asn
            245                 250                 255

Pro Glu Phe

<210> SEQ ID NO 28
<211> LENGTH: 255
<212> TYPE: PRT
<213> ORGANISM: Homo sapiens

<400> SEQUENCE: 28

Ala Ser Gln Val Gln Leu Val Gln Ser Gly Asp Glu Val Lys Lys Pro
1               5                   10                  15

Gly Ala Ser Val Lys Val Ser Cys Lys Asn Ser Gly Tyr Thr Phe Ser
            20                  25                  30

Ser His Gly Ile Ser Trp Val Arg Gln Ala Pro Gly Gln Arg Leu Glu
        35                  40                  45

Trp Met Gly Trp Ile Asn Ala Gly Asn Gly His Thr Arg Tyr Ser Gln
50                  55                  60

Lys Phe Gln Gly Arg Val Thr Ile Thr Arg Asp Thr Ser Ala Arg Met
65                  70                  75                  80

Ala Tyr Met Asp Leu Ser Ser Leu Thr Ser Asp Asp Thr Ala Val Tyr
                85                  90                  95

Tyr Cys Ala Arg Gly Gly Thr His Gly Phe Asp Tyr Trp Gly Gln
            100                 105                 110

Gly Thr Leu Val Thr Ala Ser Ser Ala Ser Thr Lys Gly Pro Ser Gly
        115                 120                 125

Ile Leu Gly Ser Gly Gly Gly Ser Gly Gly Gly Ser Gly Gly
        130                 135                 140

Gly Gly Ser Glu Ile Val Leu Thr Gln Ser Pro Gly Thr Leu Ser Leu
145                 150                 155                 160

Ser Pro Gly Asp Gly Ala Thr Leu Ser Cys Arg Ala Ser Gln Ser Val
                165                 170                 175

Ser Ser Asn Tyr Leu Ala Trp Tyr Gln Gln Ile Pro Gly Gln Ala Pro
            180                 185                 190

Arg Leu Leu Ile His Gly Ala Ser Thr Arg Ala Ser Gly Ile Pro Asp
            195                 200                 205

Arg Phe Arg Gly Ser Ala Ser Gly Thr Asp Phe Thr Leu Thr Ile Ser
        210                 215                 220

Arg Leu Glu Pro Glu Asp Phe Ala Leu Tyr Tyr Cys Gly Gln Tyr Gly
225                 230                 235                 240

Ala Ser Pro Ile Thr Phe Gly Pro Arg Gly His Arg Pro Gly Asp
            245                 250                 255

<210> SEQ ID NO 29
<211> LENGTH: 266
<212> TYPE: PRT
<213> ORGANISM: Homo sapiens

<400> SEQUENCE: 29
```

Ala Ser Met Val Gln Ser Gly Ala Glu Val Lys Lys Pro Gly Ala Ser
1               5                   10                  15

Val Lys Val Ser Cys Lys Ala Ser Gly Tyr Thr Phe Ser Ser His Gly
            20                  25                  30

Ile Ser Trp Val Arg Gln Ala Pro Gly Gln Arg Leu Glu Trp Met Gly
        35                  40                  45

Trp Ile Asn Ala Gly Asn Gly His Thr Arg Tyr Ser Gln Lys Phe Gln
    50                  55                  60

Gly Arg Val Thr Ile Thr Arg Asp Thr Ser Ala Arg Met Ala Tyr Met
65                  70                  75                  80

Asp Leu Ser Ser Leu Thr Ser Asp Asp Thr Ala Val Tyr Tyr Cys Ala
                85                  90                  95

Arg Gly Gly Gly Thr His Gly Phe Asp Tyr Trp Gly Gln Gly Thr Leu
            100                 105                 110

Val Thr Ala Ser Ser Ala Ser Thr Lys Gly Pro Ser Gly Ile Leu Gly
        115                 120                 125

Ser Gly Gly Gly Gly Ser Gly Gly Gly Ser Gly Gly Gly Gly Ser
    130                 135                 140

Glu Ile Val Leu Thr Gln Ser Pro Gly Thr Leu Ser Leu Ser Pro Gly
145                 150                 155                 160

Asp Gly Ala Thr Leu Ser Cys Arg Ala Ser Gln Ser Val Ser Ser Asn
                165                 170                 175

Tyr Leu Ala Trp Tyr Gln Gln Ile Pro Gly Gln Ala Pro Arg Leu Leu
            180                 185                 190

Ile His Gly Ala Ser Thr Arg Ala Ser Gly Ile Pro Asp Arg Phe Arg
        195                 200                 205

Gly Ser Ala Ser Gly Thr Asp Phe Thr Leu Thr Ile Ser Arg Leu Glu
    210                 215                 220

Pro Glu Asp Phe Ala Leu Tyr Tyr Cys Gly Gln Tyr Gly Arg Ser Pro
225                 230                 235                 240

Ile Thr Phe Gly Gln Gly Thr Arg Leu Glu Ile Lys Ser Gly Ile Leu
                245                 250                 255

Glu Gln Lys Leu Ile Ser Glu Glu Asp Leu
            260                 265

<210> SEQ ID NO 30
<211> LENGTH: 265
<212> TYPE: PRT
<213> ORGANISM: Homo sapiens

<400> SEQUENCE: 30

Ala Ser Gln Val Gln Leu Val Gln Ser Gly Ala Glu Val Lys Lys Pro
1               5                   10                  15

Gly Ala Ser Val Lys Val Ser Cys Lys Ala Ser Gly Tyr Thr Phe Thr
            20                  25                  30

Gly Tyr Tyr Ile His Trp Val Arg Gln Ala Pro Gly Gln Gly Leu Glu
        35                  40                  45

Trp Met Gly Arg Ile Asp Pro Asn Ser Gly Asp Thr Arg Tyr Ala Gln
    50                  55                  60

Asn Leu Gln Gly Arg Val Thr Met Thr Arg Asp Thr Ser Val Ser Thr
65                  70                  75                  80

Ala Tyr Val Glu Leu Ser Gly Leu Thr Pro Asp Asp Thr Ala Val Tyr
                85                  90                  95

Tyr Cys Ile Arg Gly Tyr Pro Met Leu Pro Ala Gly Pro Thr Trp Gly
            100                 105                 110

```
Gln Gly Thr Thr Val Thr Val Ser Ser Gly Ile Leu Gly Gly
        115                 120                 125

Gly Gly Ser Gly Gly Gly Ser Gly Gly Gly Ser Glu Ile Val
130                 135                 140

Leu Thr Gln Ser Pro Gly Thr Leu Ser Phe Ser Pro Gly Glu Arg Ala
145                 150                 155                 160

Thr Leu Ser Cys Arg Ala Ser Gln Ser Val Ser Ser Tyr Leu Ala
                165                 170                 175

Trp Tyr Gln Gln Lys Pro Gly Gln Ala Pro Arg Leu Leu Ile Tyr Gly
                180                 185                 190

Ala Ser Thr Arg Ala Thr Gly Ile Pro Asp Arg Phe Ser Gly Ser Gly
                195                 200                 205

Ser Gly Thr Asp Phe Thr Leu Thr Ile Ser Arg Leu Glu Pro Glu Asp
210                 215                 220

Phe Cys Ser Val Phe Thr Val Ser Thr Met Val Ala His Leu Ser Thr
225                 230                 235                 240

Leu Leu Ala Arg Gly Thr Lys Leu Glu Ile Lys Ser Gly Ile Leu Glu
                245                 250                 255

Gln Lys Leu Ile Ser Glu Glu Asp Leu
                260                 265

<210> SEQ ID NO 31
<211> LENGTH: 240
<212> TYPE: PRT
<213> ORGANISM: Homo sapiens

<400> SEQUENCE: 31

Ala Ser Gln Ile Thr Leu Lys Glu Ser Gly Pro Thr Leu Val Lys Pro
1               5                   10                  15

Thr Gln Thr Leu Thr Leu Thr Cys Thr Phe Ser Gly Phe Ser Leu Thr
                20                  25                  30

Thr Gly Gly Val Gly Val Gly Trp Ile Arg Gln Pro Pro Gly Lys Ala
            35                  40                  45

Leu Glu Trp Leu Ala Leu Ile Tyr Trp Asp Asp Asp Lys Arg Tyr Ser
        50                  55                  60

Pro Ser Leu Lys Ser Arg Leu Thr Ile Thr Lys Asp Thr Ser Lys Asn
65                  70                  75                  80

Gln Val Val Leu Thr Met Thr Asn Met Asp Pro Val Asp Thr Gly Thr
                85                  90                  95

Tyr Tyr Cys Ala Arg Thr Pro Ser Gly Tyr Gly Ala Tyr Asp Met
                100                 105                 110

Trp Gly Gln Gly Thr Met Val Thr Val Ser Ser Gly Ile Leu Gly Ser
            115                 120                 125

Gly Gly Gly Gly Ser Gly Gly Gly Ser Gly Gly Gly Ser Glu
130                 135                 140

Ile Val Leu Thr Gln Ser Pro Gly Thr Leu Ser Leu Ser Pro Gly Glu
145                 150                 155                 160

Arg Ala Thr Leu Ser Cys Arg Ala Ser Arg Ser Val Ser Ser Asn Tyr
                165                 170                 175

Leu Ala Trp Tyr Gln Gln Lys Pro Gly Gln Ala Pro Ser Leu Leu Ile
            180                 185                 190

Tyr Gly Ala Ser Ser Arg Ala Thr Gly Val Pro Asp Arg Phe Ser Val
                195                 200                 205

Ser Gly Ser Gly Thr Asp Phe Thr Leu Thr Ile Ser Arg Ser Gly Ser
```

```
                    210                 215                 220
Leu Asn Asp Thr Gln Cys Ile Thr Val Ser Thr Met Val Ser Arg Asp
225                 230                 235                 240

<210> SEQ ID NO 32
<211> LENGTH: 271
<212> TYPE: PRT
<213> ORGANISM: Homo sapiens

<400> SEQUENCE: 32

Ala Ser Gly Gly Gly Gly Ser Gly Gly Gly Gly Ser Gly Gly Gly Gly
1               5                   10                  15

Ser Ala Ser Gln Val Gln Leu Gln Gln Ser Gly Pro Gly Leu Val Lys
                20                  25                  30

Pro Ser Gln Thr Leu Ser Leu Thr Cys Ala Ile Ser Gly Asp Ser Val
            35                  40                  45

Ser Ser Tyr Ser Ala Ala Trp Asn Trp Ile Arg Gln Ser Pro Ser Arg
        50                  55                  60

Gly Leu Glu Trp Leu Gly Arg Thr Tyr Tyr Arg Ser Lys Trp Tyr Asn
65                  70                  75                  80

Asp Phe Ala Pro Ser Val Lys Ser Arg Ile Ser Ile Asn Pro Asp Thr
                85                  90                  95

Ser Lys Asn Gln Phe Ser Leu Gln Leu Asn Ser Val Thr Pro Glu Asp
            100                 105                 110

Thr Ala Val Tyr Tyr Cys Ala Arg Arg Gly Gln Arg Glu Arg Gly Tyr
        115                 120                 125

Phe Asp Leu Trp Gly Arg Gly Thr Leu Val Thr Val Ser Ser Gly Ile
    130                 135                 140

Leu Gly Ser Gly Gly Gly Gly Ser Gly Gly Gly Gly Ser Gly Gly Gly
145                 150                 155                 160

Gly Ser Glu Ile Val Leu Thr Gln Ser Pro Gly Thr Leu Ser Leu Ser
                165                 170                 175

Pro Gly Glu Arg Ala Thr Leu Ser Cys Arg Ala Ser Gln Ser Val Ser
            180                 185                 190

Ser Asn Tyr Leu Ala Trp Tyr Gln Gln Lys Pro Gly Gln Ala Pro Arg
        195                 200                 205

Leu Leu Ile Tyr Gly Ala Ser Ser Arg Ala Thr Gly Ile Pro Asp Arg
    210                 215                 220

Phe Ser Gly Thr Gly Ser Gly Thr Asp Phe Thr Leu Thr Ile Arg Arg
225                 230                 235                 240

Leu Glu Pro Glu Asp Phe Ala Val Tyr Tyr Cys Gln Gln Tyr Gly Ser
                245                 250                 255

Ser Leu Arg Arg Ser Ala Lys Gly Ser Asn Gly Gly Asn Gln Met
            260                 265                 270

<210> SEQ ID NO 33
<211> LENGTH: 252
<212> TYPE: PRT
<213> ORGANISM: Homo sapiens

<400> SEQUENCE: 33

Gln Asp Pro Gly Leu Val Lys Pro Ser Gln Thr Leu Ser His His Arg
1               5                   10                  15

Val Pro Ser Pro Glu Asp Ser Val Ser Ser Tyr Ser Ala Ala Trp Asn
                20                  25                  30

Trp Ile Arg Gln Ser Pro Ser Arg Gly Leu Glu Trp Leu Gly Arg Thr
```

-continued

```
                35                  40                  45
Tyr Tyr Arg Ser Lys Trp Tyr Asn Asp Phe Ala Pro Ser Val Lys Ser
 50                  55                  60

Arg Ile Ser Ile Asn Pro Asp Thr Ser Lys Asn Gln Phe Ser Leu Gln
 65                  70                  75                  80

Leu Asn Ser Val Thr Pro Glu Asp Thr Ala Val Tyr Tyr Cys Ala Arg
                 85                  90                  95

Arg Gly Gln Arg Glu Arg Gly Tyr Phe Asp Leu Trp Gly Arg Gly Thr
                100                 105                 110

Leu Val Thr Val Ser Ser Gly Ile Leu Gly Ser Gly Gly Gly Gly Ser
                115                 120                 125

Gly Gly Gly Gly Ser Gly Gly Gly Ser Glu Ile Val Leu Thr Gln
 130                 135                 140

Ser Pro Gly Thr Leu Ser Leu Ser Pro Gly Glu Arg Ala Thr Leu Ser
 145                 150                 155                 160

Cys Arg Ala Ser Gln Ser Val Ser Ser Asn Tyr Leu Ala Trp Tyr Gln
                165                 170                 175

Gln Lys Pro Gly Gln Ala Pro Arg Leu Leu Ile Tyr Gly Ala Ser Ser
                180                 185                 190

Arg Ala Thr Gly Ile Pro Asp Arg Phe Ser Gly Thr Gly Ser Gly Thr
                195                 200                 205

Asp Phe Thr Leu Thr Ile Arg Arg Leu Glu Pro Glu Asp Phe Pro Val
 210                 215                 220

Tyr Ser Cys Gln Gln Tyr Gly Ser Ser Pro Lys Thr Phe Gly Gln Gly
 225                 230                 235                 240

Ser Lys Val Glu Ile Lys Ser Gly Ile Leu Glu Ser
                245                 250

<210> SEQ ID NO 34
<211> LENGTH: 268
<212> TYPE: PRT
<213> ORGANISM: Homo sapiens

<400> SEQUENCE: 34

Ala Ser Gln Val Gln Leu Gln Gln Ser Gly Pro Gly Leu Val Lys Pro
 1               5                  10                  15

Ser Gln Thr Leu Ser Leu Thr Cys Ala Ile Ser Gly Asp Ser Val Ser
                20                  25                  30

Ser Tyr Ser Ala Ala Trp Asn Trp Ile Arg Gln Ser Pro Ser Arg Gly
                35                  40                  45

Leu Glu Trp Leu Gly Arg Thr Tyr Tyr Arg Ser Lys Trp Tyr Asn Asp
 50                  55                  60

Phe Ala Pro Ser Val Lys Ser Arg Ile Ser Ile Asn Pro Asp Thr Ser
 65                  70                  75                  80

Lys Asn Gln Phe Ser Leu Gln Leu Asn Ser Val Thr Pro Glu Asp Thr
                 85                  90                  95

Ala Val Tyr Tyr Cys Ala Arg Arg Gly Gln Arg Glu Arg Gly Tyr Phe
                100                 105                 110

Asp Leu Trp Gly Arg Gly Thr Leu Val Thr Val Ser Ser Gly Ile Leu
                115                 120                 125

Gly Ser Gly Gly Gly Gly Ser Gly Gly Gly Gly Ser Gly Gly Gly Gly
 130                 135                 140

Ser Glu Ile Val Leu Thr Gln Ser Pro Gly Thr Leu Ser Leu Ser Pro
 145                 150                 155                 160
```

```
Gly Glu Arg Ala Thr Leu Ser Cys Arg Ala Ser Gln Ser Val Ser Ser
            165                 170                 175

Asn Tyr Leu Ala Trp Tyr Gln Gln Lys Pro Gly Gln Ala Pro Arg Leu
        180                 185                 190

Leu Ile Tyr Gly Ala Ser Ser Arg Ala Thr Gly Ile Pro Asp Arg Phe
    195                 200                 205

Ser Gly Thr Gly Ser Gly Thr Asp Phe Thr Leu Thr Ile Arg Arg Leu
210                 215                 220

Glu Pro Glu Asp Phe Ala Val Tyr Tyr Cys Gln Gln Tyr Gly Ser Ser
225                 230                 235                 240

Pro Lys Thr Phe Gly Gln Gly Asn Gln Gly Asn Gln Ile Arg Lys
                245                 250                 255

Phe Tyr Glu Gln Lys Leu Ile Ser Glu Glu Asp Leu
        260                 265
```

<210> SEQ ID NO 35
<211> LENGTH: 24
<212> TYPE: DNA
<213> ORGANISM: ARTIFICIAL SEQUENCE
<220> FEATURE:
<223> OTHER INFORMATION: PCR PRIMER

<400> SEQUENCE: 35
caacaaaaaa ttgttaatat acct                                          24

<210> SEQ ID NO 36
<211> LENGTH: 22
<212> TYPE: DNA
<213> ORGANISM: ARTIFICIAL SEQUENCE
<220> FEATURE:
<223> OTHER INFORMATION: PCR PRIMER

<400> SEQUENCE: 36
gttacatcta cactgttgtt at                                            22

<210> SEQ ID NO 37
<211> LENGTH: 21
<212> TYPE: DNA
<213> ORGANISM: ARTIFICIAL SEQUENCE
<220> FEATURE:
<223> OTHER INFORMATION: PCR PRIMER

<400> SEQUENCE: 37
gtacgagcta aaagtacagt g                                             21

<210> SEQ ID NO 38
<211> LENGTH: 20
<212> TYPE: DNA
<213> ORGANISM: ARTIFICIAL SEQUENCE
<220> FEATURE:
<223> OTHER INFORMATION: PCR PRIMER

<400> SEQUENCE: 38
tagataccca tacgacgttc                                               20

<210> SEQ ID NO 39
<211> LENGTH: 20
<212> TYPE: DNA
<213> ORGANISM: ARTIFICIAL SEQUENCE
<220> FEATURE:
<223> OTHER INFORMATION: PCR PRIMER

<400> SEQUENCE: 39

```
ccgccgagct attacaagtc                                              20
```

<210> SEQ ID NO 40
<211> LENGTH: 20
<212> TYPE: DNA
<213> ORGANISM: ARTIFICIAL SEQUENCE
<220> FEATURE:
<223> OTHER INFORMATION: PCR PRIMER

<400> SEQUENCE: 40

```
tctgcaggct agtggtggtg                                              20
```